US009439789B2

(12) United States Patent
Palmaz

(10) Patent No.: US 9,439,789 B2
(45) Date of Patent: Sep. 13, 2016

(54) IMPLANTABLE MEDICAL DEVICE HAVING ENHANCED ENDOTHELIAL MIGRATION FEATURES AND METHODS OF MAKING THE SAME

(71) Applicant: Palmaz Scientific, Inc., Dallas, TX (US)

(72) Inventor: Julio C. Palmaz, Napa, CA (US)

(73) Assignee: Palmaz Scientific, Inc., Fremont, CA (US)

( * ) Notice: Subject to any disclaimer, the term of this patent is extended or adjusted under 35 U.S.C. 154(b) by 0 days.

(21) Appl. No.: 14/156,017

(22) Filed: Jan. 15, 2014

(65) Prior Publication Data
US 2014/0194974 A1 Jul. 10, 2014

Related U.S. Application Data

(63) Continuation of application No. 13/103,576, filed on May 9, 2011, now Pat. No. 8,632,583.

(51) Int. Cl.
*A61F 2/86* (2013.01)
*A61F 2/82* (2013.01)
(Continued)

(52) U.S. Cl.
CPC ............... *A61F 2/82* (2013.01); *A61F 2/0077* (2013.01); *A61F 2/86* (2013.01); *A61F 2/90* (2013.01); *A61F 2/91* (2013.01); *A61F 2/01* (2013.01); *A61F 2/06* (2013.01); *A61F 2/24* (2013.01); *A61F 2230/0017* (2013.01);

(Continued)

(58) Field of Classification Search
CPC ..................... A61F 2/0077; A61F 2002/0086; A61F 2002/0081
USPC ........... 623/1.14, 1.15, 1.16, 1.17, 1.21, 1.3, 623/1.31, 1.32, 1.33, 1.35, 1.37, 1.39–1.48
See application file for complete search history.

(56) References Cited

U.S. PATENT DOCUMENTS

| 4,425,696 | A | 1/1984 | Torniainen | 29/157.3 |
| 4,437,327 | A | 3/1984 | Madden | 72/94 |

(Continued)

FOREIGN PATENT DOCUMENTS

| EP | 0 603 959 | 6/1994 | A61F 2/06 |
| EP | 0 701 803 | 3/1996 | A61F 2/30 |

(Continued)

OTHER PUBLICATIONS

Calmar Laser, Inc., Application of fiber laser chirped pulse amplifiers (Application notes) PN 200-0400-00, Rev 1.0: pp. 1-9 (2009).

(Continued)

*Primary Examiner* — Suba Ganesan
(74) *Attorney, Agent, or Firm* — Benjamin D. Rotman; J. Peter Paredes; Rosenbaum IP, P.C.

(57) ABSTRACT

An implantable medical device having enhanced endothelial migration features, generally comprises: a structural member including a leading edge and a trailing edge interconnected by a third surface region, the leading edge including a second surface region in a generally curvilinear cross-section, and the trailing edge including a fourth surface region in a generally curvilinear cross-section, whereby blood flow over the second surface region generate shear stress at the second surface region without an eddy region in the second surface region.

20 Claims, 16 Drawing Sheets

(51) Int. Cl.
*A61F 2/90* (2013.01)
*A61F 2/91* (2013.01)
*A61F 2/00* (2006.01)
*A61F 2/01* (2006.01)
*A61F 2/06* (2013.01)
*A61F 2/24* (2006.01)

(52) U.S. Cl.
CPC ............... *A61F 2230/0026* (2013.01); *A61F 2230/0056* (2013.01); *A61F 2250/0051* (2013.01); *Y10T 29/49* (2015.01); *Y10T 29/49826* (2015.01)

(56) References Cited

U.S. PATENT DOCUMENTS

| | | | |
|---|---|---|---|
| 4,657,544 A | 4/1987 | Pinchuk | 623/1 |
| 4,733,665 A | 3/1988 | Palmaz | 128/343 |
| 5,102,417 A | 4/1992 | Palmaz | 606/195 |
| 5,133,845 A | 7/1992 | Vallana et al. | 204/192.15 |
| 5,195,984 A | 3/1993 | Schatz | 606/195 |
| 5,207,709 A | 5/1993 | Picha | 623/11 |
| 5,278,063 A | 1/1994 | Hubbell et al. | 435/240.243 |
| 5,370,684 A | 12/1994 | Vallana et al. | 623/1 |
| 5,387,247 A | 2/1995 | Vallana et al. | 623/66 |
| 5,423,885 A | 6/1995 | Williams | 623/1 |
| 5,510,628 A | 4/1996 | Georger, Jr. et al. | 257/32 |
| 5,607,463 A | 3/1997 | Schwartz et al. | 623/1 |
| 5,649,951 A | 7/1997 | Davidson | 606/198 |
| 5,690,670 A | 11/1997 | Davidson | 606/198 |
| 5,718,713 A | 2/1998 | Frantzen | 606/198 |
| 5,725,573 A | 3/1998 | Dearnaley et al. | 623/2 |
| 5,733,303 A | 3/1998 | Israel et al. | 606/198 |
| 5,735,896 A | 4/1998 | Amon et al. | 623/11 |
| 5,772,864 A | 6/1998 | Moller | 205/73 |
| 5,782,908 A | 7/1998 | Cahalan et al. | 623/1 |
| 5,843,289 A | 12/1998 | Lee et al. | 204/192.3 |
| 5,855,802 A | 1/1999 | Acciai et al. | 216/8 |
| 5,891,507 A | 4/1999 | Jayaraman | 427/2.25 |
| 5,895,419 A | 4/1999 | Tweden et al. | 623/2 |
| 5,897,911 A | 4/1999 | Loeffler | 427/2.25 |
| 5,932,299 A | 8/1999 | Katoot | 427/508 |
| 5,955,588 A | 9/1999 | Tsang et al. | 536/21 |
| 6,001,622 A | 12/1999 | Dedhar et al. | 435/194 |
| 6,027,526 A | 2/2000 | Limon et al. | 623/1 |
| 6,077,413 A | 6/2000 | Hafeli et al. | 205/170 |
| 6,086,773 A | 7/2000 | Dufresne et al. | 216/8 |
| 6,103,320 A | 8/2000 | Matsumoto et al. | 427/535 |
| 6,140,127 A | 10/2000 | Sprague | 435/395 |
| 6,143,370 A | 11/2000 | Panagiotou et al. | 427/422 |
| RE36,991 E | 12/2000 | Yamamoto et al. | 204/192.15 |
| 6,183,255 B1 | 2/2001 | Oshida | 433/201.1 |
| 6,190,404 B1 | 2/2001 | Palmaz et al. | 623/1.15 |
| 6,192,944 B1 | 2/2001 | Greenhalgh | 139/425 R |
| 6,207,536 B1 | 3/2001 | Matsumoto et al. | 438/478 |
| 6,253,441 B1 | 7/2001 | Wheat et al. | 29/527.2 |
| 6,258,121 B1 | 7/2001 | Yang et al. | 623/1.46 |
| 6,274,014 B1 | 8/2001 | Matsumoto et al. | 204/298.11 |
| 6,280,467 B1 | 8/2001 | Leonhardt | 623/1.16 |
| 6,325,825 B1 | 12/2001 | Kula et al. | 623/1.3 |
| 6,334,868 B1 | 1/2002 | Ham | 623/1.13 |
| 6,379,383 B1 | 4/2002 | Palmaz et al. | 623/1.49 |
| 6,395,326 B1* | 5/2002 | Castro et al. | 427/2.24 |
| 6,432,128 B1 | 8/2002 | Wallace et al. | 623/1.11 |
| 6,475,233 B2 | 11/2002 | Trozera | 623/1.15 |
| 6,514,261 B1 | 2/2003 | Randall et al. | 606/108 |
| 6,520,923 B1 | 2/2003 | Jalisi | 600/585 |
| 6,527,919 B1 | 3/2003 | Roth | 204/192.15 |
| 6,527,938 B2 | 3/2003 | Bales et al. | 205/229 |
| 6,533,905 B2 | 3/2003 | Johnson et al. | 204/192.15 |
| 6,537,202 B1 | 3/2003 | Frantzen | 600/36 |
| 6,537,310 B1 | 3/2003 | Palmaz et al. | 623/1.13 |
| 6,652,579 B1 | 11/2003 | Cox et al. | 623/1.34 |
| 6,685,737 B1 | 2/2004 | Pacetti | 623/1.15 |
| 6,689,473 B2 | 2/2004 | Guire et al. | 428/412 |
| 6,820,676 B2 | 11/2004 | Palmaz et al. | 623/1.49 |
| 6,849,085 B2 | 2/2005 | Marton | 623/1.13 |
| 8,037,733 B2 | 10/2011 | Banas et al. | 72/370.04 |
| 2001/0001834 A1 | 5/2001 | Palmaz et al. | 623/1.15 |
| 2001/0010014 A1 | 7/2001 | Trozera | 623/1.16 |
| 2001/0039454 A1 | 11/2001 | Ricci et al. | 623/23.5 |
| 2002/0016623 A1 | 2/2002 | Kula et al. | 623/1.11 |
| 2002/0017503 A1* | 2/2002 | Banas et al. | 219/69.11 |
| 2002/0156522 A1 | 10/2002 | Ivancev et al. | 623/1.13 |
| 2002/0193336 A1 | 12/2002 | Elkins et al. | 514/44 |
| 2003/0028246 A1 | 2/2003 | Palmaz et al. | 623/1.49 |
| 2003/0105512 A1 | 6/2003 | Kanesaka | 623/1.15 |
| 2003/0130718 A1 | 7/2003 | Palmaz et al. | 623/1.12 |
| 2003/0139801 A1* | 7/2003 | Sirhan et al. | 623/1.15 |
| 2004/0014253 A1 | 1/2004 | Gupta et al. | 438/48 |
| 2004/0133265 A1 | 7/2004 | Duffy | 623/1.16 |
| 2005/0055085 A1 | 3/2005 | Rivron et al. | 623/1.39 |
| 2005/0102036 A1 | 5/2005 | Bartee et al. | 623/23.76 |
| 2005/0119723 A1 | 6/2005 | Peacock, III | 623/1.15 |
| 2006/0178751 A1 | 8/2006 | Despres, III et al. | 623/23.5 |
| 2007/0225823 A1 | 9/2007 | Hawkins et al. | 623/23.51 |
| 2008/0140179 A1* | 6/2008 | Ladisa | 623/1.11 |
| 2008/0183276 A1 | 7/2008 | Melder | 623/1.15 |
| 2009/0099652 A1* | 4/2009 | Granada | A61F 2/91 623/1.46 |
| 2011/0091515 A1 | 4/2011 | Zilberman et al. | 424/409 |

FOREIGN PATENT DOCUMENTS

| | | | |
|---|---|---|---|
| EP | 0 734 699 | 11/1996 | A61F 2/06 |
| EP | 0 815 806 | 1/1998 | A61F 2/06 |
| EP | 0 850 604 | 1/1998 | A61F 2/06 |
| EP | 0 974 314 | 1/2000 | A61F 2/06 |
| EP | 1 028 672 | 6/2005 | A61F 2/06 |
| JP | 07-284527 | 10/1995 | A61F 27/00 |
| JP | 09-225021 | 9/1997 | A61L 27/00 |
| JP | 63-502405 | 9/1998 | A61L 33/00 |
| JP | 2001-294411 | 10/2001 | C01B 25/32 |
| JP | 2002-017847 | 1/2002 | A61L 27/00 |
| WO | WO95/12472 | 5/1995 | B23K 26/02 |
| WO | WO98/45506 | 10/1998 | C25D 7/04 |
| WO | WO99/23977 | 5/1999 | A61F 2/06 |
| WO | WO00/10623 | 3/2000 | A61F 31/14 |
| WO | WO01/00112 | 1/2001 | A61F 2/06 |
| WO | WO01/35865 | 5/2001 | A61F 2/06 |
| WO | WO01/68158 | 9/2001 | A61L 27/08 |
| WO | WO01/74274 | 10/2001 | A61F 2/06 |
| WO | WO01/76525 | 10/2001 | A61F 2/06 |
| WO | WO01/87371 | 11/2001 | A61L 27/42 |
| WO | WO01/89420 | 11/2001 | A61F 2/06 |
| WO | WO 2008/150719 | 12/2008 | A61F 2/90 |
| WO | WO 2009/070624 | 6/2009 | A61F 2/06 |
| WO | WO2009/070624 | 6/2009 | A61F 2/06 |

OTHER PUBLICATIONS

Chen, C., et al., "Reports: Geometric Control of Cell Life and Death" *Science* 276(5317): 1425-1428 (1997).

Chu, P.K., et al., "Plasma-surface modification of biomaterials" *Materials Science and Engineering* R 36: 143-206 (2002).

Davies, P.F., et al., "Endothelial cell adhesion in real time" The Journal of Clinical Investigation 91: 2640-2652 (1993).

Davies, P.F., et al., "Quantitative studies of endothelial cell adhesion" *The Journal of Clinical Investigation*, 93: 2031-2038 (1994).

Dehlaghi, V., et al., "Numerical analysis of pulsatile blood flow in a stented human coronary artery with a flow divider" *Am. J. of Applied Sciences* 4(6): 397-404 (2007).

Den Braber, E.T., et al., "Effects of parallel surface microgrooves and surface energy on cell growth" *Journal of Biomedical Materials Research* 29: 511-518 (1995).

Giancotti, F.G., et al., "Review integrin signaling" Science 285(5430): 1028-1032 (1999).

Hehrlein, C., et al., "Therapy and prevention: Influence of surface texture and charge on the biocompatibility of endovascular stents" University of Heidelberg, Germany; Dept. of Cardiology, *Antatomy and Physical Chemistry*, pp. 581-585 (1995).

(56) References Cited

OTHER PUBLICATIONS

Holleck, H., et al., "Multilayer PVD coatings for wear protection" *Surface and Coatings Technology* 76-77(1): 328-336 (1997) Abstract Only.

Kasemo, B., "Biomaterial and implant surfaces: On the role of cleanliness, contamination, and preparation procedures" J. Biomed. Mater Res.: Applied Biomaterials 22(A2): 145-158 (1988).

Kasemo, B., "Biological surface science" *Surface Science* 500: 656-677 (2002).

Kazmierska, K., et al., "Bioactive coatings for minimally invasive medical devices: Surface modification in the service of medicine" *Recent Patents on Biomedical Engineering* 2: 1-14 (2009).

LaDisa, Jr., J.F., et al., "Alterations in wall shear stress predict sites of neointimal. hyperplasia after stent implantation in rabbit iliac arteries" *Am. J. Physiol. Heart Circ. Physiol.*, 288: H2465-H2475 (2005).

LaDisa Jr., J.F., et al., "Axial stent strut angle influences wall shear stress after stent implantation: analysis using 3D computational fluid dynamics models of stent foreshortening" *Biomedical Engineering OnLine* 4(59): 1-11 (2005).

Liang, C., et al., "Preparation of porous microstructures on NiTi alloy surface with femtosecond laser pulses" *Chinese Science Bulletin* 53(5): 700-705 (2008).

Liu, X., et al., "Surface modification of titanium, titanium alloys, and related materials for biomedical applications" *Materials Science and Engineering* R 47: 49-121 (2004).

Loh, I., "Plasma surface modification in biomedical applications" *AST Technical Journal*, pp. 1-6 (undated).

Matsuda, T., "Control of cell adhesion, migration and orientation on photochemically microprocessed surfaces" *Journal of Biomedical Materials Research* 32: 165-173 (1996).

Palmaz, J., et al., "New advances in endovascular technology" *Texas Heart Institute Journal* 24(3): 156-159 (1997).

Palmaz, J., et al., "Influence of stent design and material composition on procedure outcome" *Journal of Vascular Surgery* 36(5): 1031-1039 (2002).

Sprague, E., et al., "Electrostatic forces on the surface of metals as measured by atomic force microscopy" *J. Long Term Eff Med Implants*, 10(1-2): 111-125 (2000).

Stone, P.H., et al., "Effect of endothelial shear stress on the progression of coronary artery disease, vascular remodeling, and in-stent restenosis in humans" *Circulation* 108: 438-444 (2003).

Raydiance, Inc., "Athermal ablation of nitinol for stent manufacturing" *Raydiance Application Spotlight* pp. 1-6 (2009).

Tanous, A.C., "Laser cutting takes the heat out of stent manufacturing" *Industrial Laser Solutions* pp. 20-23 (Jan./Feb. 2010).

Van der Giessen, W.J., et al., "Marked inflammatory sequel to implantation of biodegradable and nonbiodegradable polymers in porcine coronary arteries" *Circulation* 94(7): 1690-1697 (1996).

Zarbakhsh, A., "Characterization of photon-controlled titanium oxide surfaces" *ISIS Experimental Report, Rutherford Appelton Laboratory*, www.isis.rl.ac.uk/isis2001/reports/11144.pdf (2000).

Zheng, H.Y., et al., "Femtosecond laser processing of nitinol" *Applied Surface Science* 228: 201-206 (2004).

Zheng, H.Y., et al., "Ultrashort pulse laser micromachined microchannels and their application in an optical switch" *Int J Adv Manuf Technol* 27: 925-929 (2006).

European Extended Search Report issued in a corresponding foreign application, pp. 1-11 (Oct. 1, 2014).

\* cited by examiner

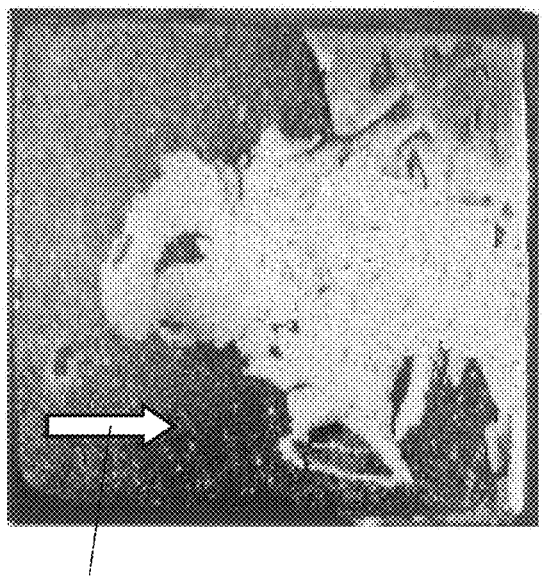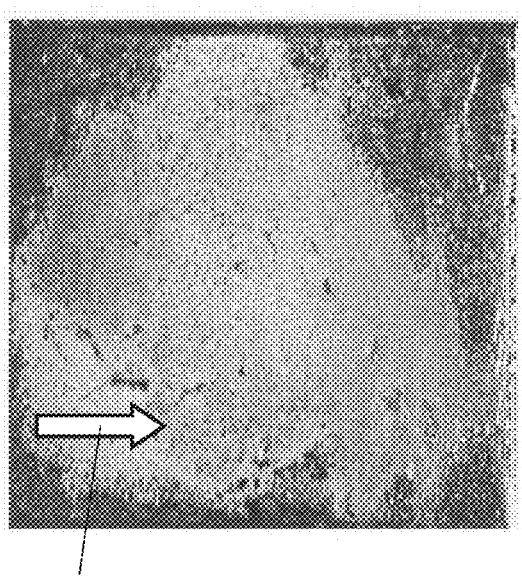
Direction of Flow  FIG. 16A        Direction of Flow  FIG. 16B
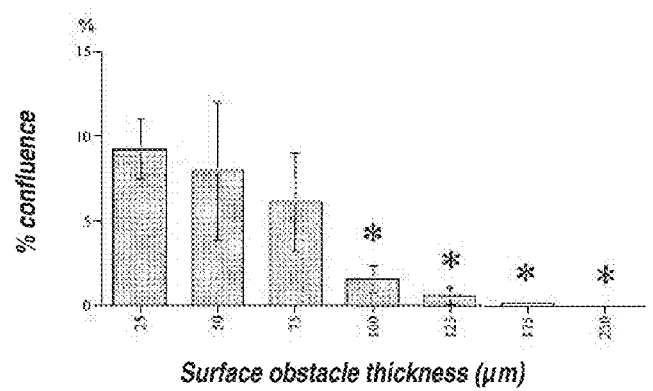
FIG. 17

IMPLANTABLE MEDICAL DEVICE HAVING ENHANCED ENDOTHELIAL MIGRATION FEATURES AND METHODS OF MAKING THE SAME

CROSS-REFERENCE TO RELATED APPLICATIONS

This application is a continuation of U.S. patent application Ser. No. 13/103,576, which was filed on May 9, 2011, and is hereby incorporated in its entirety.

BACKGROUND OF THE INVENTION

The present invention relates generally to implantable medical devices and more particularly to controlling surface properties of implantable biocompatible materials suitable for fabrication of implantable medical devices.

Implantable medical devices are fabricated of materials that are sub-optimal in terms of the biological response they elicit in vivo. Many conventional materials used to fabricate implantable devices, such as titanium, polytetrafluoroethylene, silicone, carbon fiber and polyester, are used because of their strength and physiologically inert characteristics. However, tissue integration onto these materials is typically slow and inadequate. Certain materials, such as silicone and polyester, elicit a significant inflammatory, foreign body response that drives fibrous encapsulation of the synthetic material. The fibrous encapsulation may have significant adverse effects on the implant. Moreover, conventional biomaterials have proved inadequate in eliciting a sufficient healing response necessary for complete device integration into the body. For example, in devices that contact blood, such as stents and vascular grafts, attempts to modify such devices to promote endothelial cell adhesion may have a concomitant effect of making the devices more thrombogenic.

When implanted, conventional blood-contacting implantable devices, such as stents, stent-grafts, grafts, valves, shunts and patches, fail to develop a complete endothelial layer, thereby exposing the device material to thrombus formation or smooth muscle cell proliferation, and ultimate failure of the implanted device. It has been recognized that, when implanted into the body, metals are generally considered to have superior biocompatibility than polymers used to fabricate commercially available polymeric grafts.

In investigating cellular interactions with prosthetic material surfaces, it has been found that cell adhesion to the material surface is mediated by integrins present on cell membranes that interact with the prosthetic surface. Integrins are the most prominent member of a class of extracellular matrix (ECM) adhesion receptors. Integrins are a large family of heterodimeric transmembrane proteins with different $\alpha$ and $\beta$ subunits. Integrins are regulated at several levels. Modulation of the affinity of the adhesion receptor for ligand, termed affinity modulation, is a mechanism for activation of platelet aggregation and is believed to underlie activation of leukocyte adhesion. Adhesive strengthening by clustering of adhesion receptors or by cytoskeletal-dependent processes such as cell spreading has been shown to be crucial for strong cellular attachment, control of cell growth and cell motility. Under high shear forces present in flowing blood, leukocytes first tether, then roll along the vessel surface. When a local signal, e.g., a cytokine, is released in their vicinity, the leukocyte arrests, develops a firm adhesion then migrates across the endothelium. Tethering, rolling, arrest and adhesion tightening are all known to result from activation of leukocyte integrins.

Once adhered to a surface, cell spreading and migration are associated with assembly of focal adhesion junctions. Cell migration entails the coordination of cytoskeletal-mediated process extension, i.e., filopodia and lamellopodia, formation of adhesive contacts at the leading edge of a cell, breaking adhesive contacts, and cytoskeletal retraction at the trailing edge of the cell. Focal adhesions are comprised of integrins as the major adhesion receptors along with associated cytoplasmic plaque proteins. Assembly of focal adhesions is regulated by extracellular ligand binding events and by intracellular signaling events. Ligand binding controls localization of $\beta 1$- and $\beta 3$-containing integrins into focal adhesions. The cytoplasmic domains of the $\beta$ subunits have intrinsic signals for focal adhesion localization, but incorporation of the integrins into focal adhesions is prevented by the $\alpha$ subunits of the heterodimers. Ligand binding, however, relieves this inhibition and allows the subunit cytoplasmic tail signals to recruit the integrin dimmer into the focal adhesion.

Attempts at coating implanted metal devices, such as stents, with proteins that contain the Arg-Gly-Asp (RGD) attachment site have been made with some success. The RGD sequence is the cell attachment site of a large number of adhesive extracellular matrix, blood, and cell surface proteins and many of the known integrins recognize the RGD sequence in their adhesion protein ligands. Integrin-binding activity may also be reproduced by synthetic peptides containing the RGD sequence. However, bare metal implanted materials will not, of course, have native RGD attachment sites. Thus, metal implantable devices, such as stents, have been derivitized with polymers having RGD attachment sites bound to the polymer matrix.

It has been found that when prosthetic materials are implanted, integrin receptors on cell surfaces interact with the prosthetic surface. When cells come into contact with the extracellular matrix, such as a prosthetic surface, their usual response is to extend filopodia, and integrins at the tip of the filopodia bind to the extracellular matrix and initiate the formation of focal adhesions. Actin-rich lamellipodia are generated, often between filopodia, as the cell spreads on the extracellular matrix. Fully developed focal adhesions and associated actin stress fibers ensue. These same evens occur during cell migration as cells extend lamellipodia and form focal adhesions to derive the traction necessary for movement. Giancotti, F. G., et al. *Science,* 285:13 August 1999, 1028-1032.

The integrin receptors are specific for certain ligands in vivo. If a specific protein is adsorbed on a prosthetic surface and the ligand exposed, cellular binding to the prosthetic surface may occur by integrin-ligand docking. It has also been observed that proteins bind to metals in a more permanent fashion than they do to polymers, thereby providing a more stable adhesive surface. The conformation of proteins coupled to surfaces of most medical metals and alloys appears to expose greater numbers of ligands and attract endothelial cells having surface integrin clusters to the metal or alloy surface, preferentially over leukocytes.

Because of their greater adhesive surface profiles, metals are also susceptible to short-term platelet activity and/or thrombogenicity. These deleterious properties may be offset by administration of pharmacologically active antithrombogenic agents in routine use today. Surface thrombogenicity usually disappears 1-3 weeks after initial exposure. Antithrombotic coverage is routinely provided during this period of time for coronary stenting. In non-vascular applications such as musculoskeletal and dental, metals have also greater tissue compatibility than polymers because of similar molecular considerations. The best article to demonstrate the fact that all polymers are inferior to metals is van der Giessen, W J. et al. *Marked inflammatory sequelae to implantation of biodegradable and non-biodegradable polymers in porcine coronary arteries*, Circulation, 1996:94(7): 690-7.

Normally, endothelial cells (EC) migrate and proliferate to cover denuded areas until confluence is achieved. Migration, quantitatively more important than proliferation, is affected by exposure of the EC to blood flow. Under static conditions or in the presence of minor shear stress, for example, about 1.5 dynes/cm$^2$, EC have been observed to migrate at speeds between about 10 μm/hr to about 15 μm/hr. Palmaz, J. C., Bailey, S., Marton, D., and Sprague, E. *Influence of stent design and material composition on procedure outcome* J. Vasc. Surg. 2002; 36:1031-1039. Also, the cause of restenosis includes vessel injury due to pressure from stent expansion and neointimal thickening due to decrease in vessel wall shear stress (WSS).

EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules. An EC has roughly 16-22% of its cell surface represented by integrin clusters. Davies, P. F., Robotewskyi A., Griem M. L. *Endothelial cell adhesion in real time*. J. Clin. Invest. 1993; 91:2640-2652, Davies, P. F., Robotewski, A., Griem, M. L., *Qualitiative studies of endothelial cell adhesion*, J. Clin. Invest. 1994; 93:2031-2038. This is a dynamic process, which involves more than 50% remodeling in 30 minutes.

The focal adhesion contacts vary in size and distribution, but 80% of them measure less than 6 μm$^2$, with the majority of them being about 1 μm$^2$, and tend to elongate in the direction of flow and concentrate at leading edges of the cell. Although the process of recognition and signaling to determine specific attachment receptor response to attachment sites is not completely understood, availability of attachment sites will favorably influence attachment and migration. It is known that materials commonly used as medical grafts, such as polymers, do not become covered with EC and therefore do not heal after they are placed in the arteries. Furthermore, heterogeneities of materials in contact with blood flow are preferably controlled by using vacuum deposited materials.

There have been numerous attempts to increase endothelialization of implanted medical devices such as stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene (U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299). However, all these approaches do not address the lack of endothelialization of polymer grafts.

Overall rate to reach confluence for the endothelial cells on the blood contact surface of implanted medical device is mainly determined by two factors, the rate of cell movement and rate of cell proliferation, with the first being more important. The rate of cell movement further comprises three interrelated steps. Initially, a cell forms lamellipodia and filopodia that protrude outward. This step involves reassembly of actins in the forefront of lambaepolia. After protrusion of lamellipodia from one or multiple points from the cell membrane, the front end of the lamellipodia will form a close attachment, called focal adhesion point, to the substratum through the interaction of integrin on the cell membrane and extracellular matrix binding site. The final step of cell movement involves the contraction of the posterior end through the action of myosin II. The formation of a focal adhesion point is critical for the cell movement because the protruding lamellipodia will otherwise fold back. Without the tension force from the focal adhesion point, a cell loses the contraction from the posterior end and hence stops moving.

Availability of attachment sites on the substratum is not only important for the focal adhesion point formation, but also important for propagation. It has been shown that when cells are forced to spread, they survive better and proliferate faster than cells that are confined to the same amount of surface area (*Science* 276:1425-1428, 1997). This may explain why spreading of neighbor cells stimulate a cell to proliferate, after cells are lost from epithelium.

The formation of extracellular matrix (ECM) is, to much extent, determined by the cells within it because molecules which form ECM are secreted by the cells. Subsequently, the structure of the ECM, and hence the distribution of attachment sites on the ECM for the integrin binding, determines the focal adhesion point formation, the critical step in cell movement. Therefore, proper distribution of integrin binding sites on the surface of an implanted medical device substantially determines the speed of reendothelization from the ends surrounding the device.

There still remains a need for a medical device that stimulates endothelial proliferation and movement when implanted in order to form an endothelial layer over the medical device. Furthermore, there is a remaining need for a method of fabricating such a medical device.

SUMMARY OF THE INVENTION

In one embodiment, an implantable medical device having enhanced endothelial migration features, comprises: a structural member including a leading edge and a trailing edge interconnected by a third surface region, the leading edge including a second surface region in a generally curvilinear cross-section, and the trailing edge including a fourth surface region in a generally curvilinear cross-section, whereby blood flow over the second surface region generate shear stress at the second surface region without an eddy region in the second surface region.

In another embodiment, the implantable biocompatible material includes a plurality of geometrically functional features. In one embodiment, the implantable biocompatible material includes a plurality of grooves disposed on at least one of the trailing edge, leading edge, and surface regions of the structural member.

In a further embodiment, a method of forming an implantable medical device having enhanced endothelial migration features, comprises: forming a structural member including a leading edge and a trailing edge interconnected by a third surface region, the leading edge including a second surface region in a generally curvilinear cross-section, and the trailing edge including a fourth surface region in a generally curvilinear cross-section, whereby blood flow over the second surface region generate shear stress at the second surface region without an eddy region in the second surface region.

The foregoing and other features and advantages of the disclosure are apparent from the following detailed description of exemplary embodiments, read in conjunction with the accompanying drawings; wherein like structural or functional elements are designated by like reference numerals.

BRIEF DESCRIPTION OF THE FIGURES

FIGS. 16A-16B are photographs of human aortic EC migration onto 1×1-cm, 316L stainless steel flat coupons after fixation and Giemsa staining, where entire sheet then was placed into parallel plate flow chamber and exposed to fluid-imposed arterial level shear (15 dynes/cm$^2$), as shown in FIG. 16A, and low shear (1.5 dynes/cm$^2$), as shown in FIG. 16B, wall stress on right for 4 days, and the arrow indicates that direction of flow.

FIG. 17 is a graph showing the percentage of total area of surface obstacles covered by ECs after 4 days with flow at 15 dynes/cm$^2$; where ECs were grown to confluence on polyester film sheet with attached pieces of polyester film of increasing thickness serving as obstacles; and Asterisks indicate statistically significant difference compared with 25 µm.

The foregoing and other features and advantages of the disclosure are apparent from the following detailed description of exemplary embodiments, read in conjunction with the accompanying drawings; wherein like structural or functional elements are designated by like reference numerals.

DETAILED DESCRIPTION OF THE PREFERRED EMBODIMENTS

Figure 1:
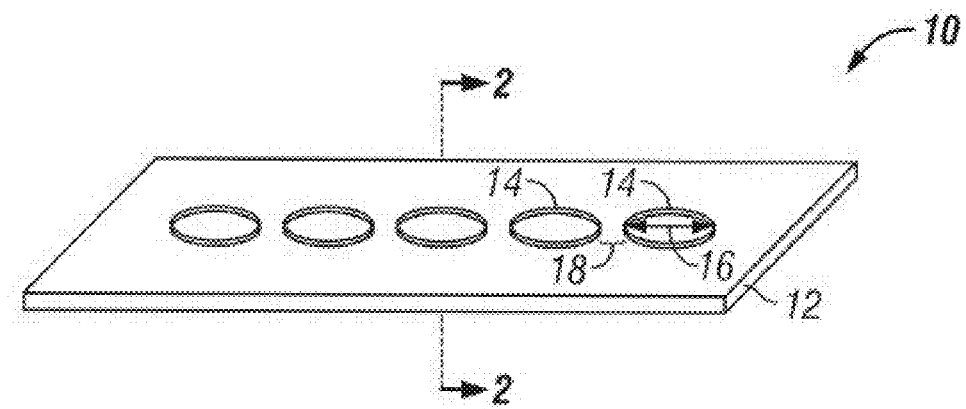
FIG. 1 is a perspective view of an embodiment including evenly distributed elevated geometric physiologically functional features on the surface of an implantable material.

In accordance with the embodiments disclosed herein, the capacity for complete endothelialization of conventional implantable materials, including metals and polymers, may be enhanced by imparting a pattern of chemically and/or physiochemically active geometric physiologically functional features onto a blood contacting surface of the implantable material. The inventive implantable devices may be fabricated of polymers, pre-existing conventional wrought metallic materials, such as stainless steel or nitinol hypotubes, or may be fabricated by thin film vacuum deposition techniques. In accordance with one embodiment, the inventive implantable materials may be vacuum deposited and resulting devices by vacuum deposition of either or both of the base implant material and the chemically and/or physiochemically active geometric physiologically functional features. Vacuum deposition permits greater control over many material characteristics and properties of the resulting material and formed device. For example, vacuum deposition permits control over grain size, grain phase, grain material composition, bulk material composition, surface topography, mechanical properties, such as transition temperatures in the case of a shape memory alloy. Moreover, vacuum deposition processes will permit creation of devices with greater material purity without the introduction of large quantities of contaminants that adversely affect the material and, therefore, the mechanical and/or biological properties of the implanted device. Vacuum deposition techniques also lend themselves to fabrication of more complex devices than those that are manufactured by conventional cold-working techniques. For example, multi-layer structures, complex geometrical configurations, extremely fine control over material tolerances, such as thickness or surface uniformity, are all advantages of vacuum deposition processing.

In vacuum deposition technologies, materials are formed directly in the desired geometry, e.g., planar, tubular, etc. The common principle of vacuum deposition processes is to take a material in a minimally processed form, such as pellets or thick foils, known as the source material and atomize them. Atomization may be carried out using heat, as is the case in physical vapor deposition, or using the effect of collisional processes, as in the case of sputter deposition, for example. In some forms of deposition a process such as laser ablation, which creates microparticles that typically consist of one or more atoms, may replace atomization; the number of atoms per particle may be in the thousands or more. The atoms or particles of the source material are then deposited on a substrate or mandrel to directly form the desired object. In other deposition methodologies, chemical reactions between ambient gas introduced into the vacuum chamber, i.e., the gas source, and the deposited atoms and/or particles are part of the deposition process. The deposited material includes compound species that are formed due to the reaction of the solid source and the gas source, such as in the case of chemical vapor deposition. In most cases, the deposited material is then either partially or completely removed from the substrate, to form the desired product.

A first advantage of vacuum deposition processing is that vacuum deposition of the metallic and/or pseudometallic films permits tight process control and films may be deposited that have a regular, homogeneous atomic and molecular pattern of distribution along their fluid-contacting surfaces. This avoids the marked variations in surface composition, creating predictable oxidation and organic adsorption patterns and has predictable interactions with water, electrolytes, proteins and cells. In particular, EC migration is supported by a homogeneous distribution of binding domains that serve as natural or implanted cell attachment sites in order to promote unimpeded migration and attachment.

Secondly, in addition to materials and devices that are made of a single metal or metal alloy layer, the inventive grafts may be comprised of a layer of biocompatible material or of a plurality of layers of biocompatible materials formed upon one another into a self-supporting multilayer structure because multilayer structures are generally known to increase the mechanical strength of sheet materials, or to provide special qualities by including layers that have special properties such as superelasticity, shape memory, radio-opacity, corrosion resistance, etc. A special advantage of vacuum deposition technologies is that it is possible to deposit layered materials and thus films possessing exceptional qualities may be produced (cf., H. Holleck, V. Schier: *Multilayer PVD coatings for wear protection*, Surface and Coatings Technology, Vol. 76-77 (1995) pp. 328-336). Layered materials, such as superstructures or multilayers, are commonly deposited to take advantage of some chemical, electronic, or optical property of the material as a coating; a common example is an antireflective coating on an optical lens. Multilayers are also used in the field of thin film fabrication to increase the mechanical properties of the thin film, specifically hardness and toughness.

Thirdly, the design possibilities for possible configurations and applications of the inventive graft are greatly realized by employing vacuum deposition technologies. Specifically, vacuum deposition is an additive technique that lends itself toward fabrication of substantially uniformly thin materials with potentially complex three dimensional geometries and structures that cannot be cost-effectively achieved, or in some cases achieved at all, by employing conventional wrought fabrication techniques. Conventional wrought metal fabrication techniques may entail smelting, hot working, cold working, heat treatment, high temperature annealing, precipitation annealing, grinding, ablation, wet etching, dry etching, cutting and welding. All of these processing steps have disadvantages including contamination, material property degradation, ultimate achievable configurations, dimensions and tolerances, biocompatibility and cost. For example conventional wrought processes are not suitable for fabricating tubes having diameters greater than about 20 mm, nor are such processes suitable for fabricating materials having wall thicknesses down to about 1 µm with sub-µm tolerances.

The embodiments disclosed herein takes advantage of the discovered relationship between chemically or physio-chemically-active geometric physiologically functional features defined and distributed on a blood contact surface and enhanced endothelial cell binding, proliferation and migration over the blood contact surface of the implantable material. The embodiments disclosed herein involves focal adhesion point formation during cellular movement and the well-established observation known as anchorage dependence, that spreading cells proliferate faster than non-spreading cells. The addition of a patterned array of geometric physiologically functional features having a hydrophobic, hydrophilic or surface energy difference relative to the surface onto which the geometric physiologically functional features are added, enhances the binding, proliferation and migration of endothelial cells to and between the geometric physiologically functional features and across the surface.

The geometric physiologically functional features disclosed herein may be formed on, in, or through one or more layers of vacuum deposited biocompatible material. In a first embodiment, the one or more layers of vacuum deposited biocompatible material are deposited on a layer of bulk material. In a second embodiment, a plurality of layers of vacuum deposited biocompatible material is deposited on one another to form a self-supporting multilayer structure. Each of the first and second embodiments includes several aspects. In a first aspect, the geometric physiologically functional features may have a non-zero thickness corresponding to a thickness of one or more layers of the vacuum deposited material. Alternatively, in other aspects, the geometric physiologically functional features may have a zero thickness or a thickness greater than one or more layers of the vacuum deposited material.

Below about 3 µm in thickness, the interactions between endothelial cells and the geometric physiologically functional features are primarily chemical and electrochemical. Geometric physiologically functional features having thicknesses greater than 3 µm and up to about 20 µm may also be employed, it being understood that as the thickness of the geometric physiologically functional feature increases there is a decreasing chemical and/or electrochemical interaction between the geometric physiologically functional feature and the endothelial cells and an increasing physical interaction (topographic guidance effect).

Additionally, it has been found that by employing UV irradiation to oxidized titanium or titanium-alloy surfaces, photochemical alteration of the surface titanium oxides alter the hydrophobicity of the exposed titanium oxides and act as affinity binding and migration sites for endothelial cell attachment and proliferation across a titanium or titanium-alloy surface. Where UV irradiation is employed, the thickness of the photochemically altered regions of titanium oxide are, for all practical purposes, 0 µm. Thus, within the context of the present application, the term "geometric physiologically functional features" is intended to include both physical members and photochemically-altered regions having thicknesses down to 0 µm.

In FIG. 1, a portion of an implantable material 10 showing the surface 12 with described elevated geometric physiologically functional features 14 is illustrated. The geometric physiologically functional features are elevated from the surface of the implantable material to a height ranging from about 1 nm to about 20 µm. Preferably, the height of the geometric physiologically functional feature 14 ranges from about 1 nm to about 3 µm. The shape of geometric physiologically functional features can be either circular, square, rectangle, triangle, parallel lines, straight or curvilinear lines or any combination thereof. Each of the geometric physiologically functional features is preferably from about 1 nm to about 75 µm, and preferably from about 1 nm to about 50 µm in feature width 16, or feature diameter if the geometric physiologically functional feature is circular. A gap distance 18 between each of the geometric physiologically functional features may be less than, about equal to or greater than the feature width 16, i.e., between about 1 nm to about 75 µm edge-to-edge.

Figure 2:
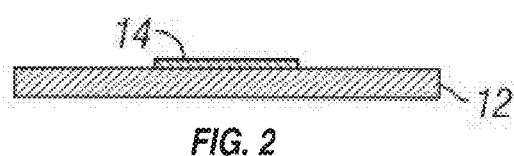
FIG. 2 is cross-sectional view of FIG. 1 along line 2-2.

FIG. 2 is a cross-sectional view along line 2-2 in FIG. 1. One of the elevated geometric physiologically functional features 14 is shown on the surface 12 of the implantable material.

Figure 3:
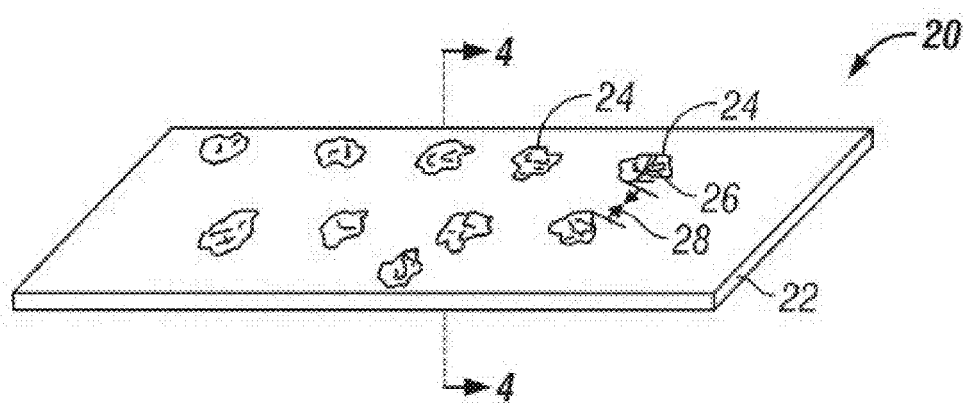
FIG. 3 is a perspective view of an embodiment including evenly distributed chemically defined geometric physiologically functional features on the surface of an implantable material.

In FIG. 3, a layer of a titanium or titanium-alloy material 20 is heating to oxidize and form titanium dioxide on the surface of the material 20. In one embodiment, the layer of titanium or titanium-alloy material 20 is deposited over one or more layers of vacuum deposited material in a self-supporting multilayer structure. In another embodiment, the layer of titanium or titanium-alloy material 20 is deposited over a bulk material that may have one or more layers of vacuum deposited material deposited thereon.

The geometric physiologically functional features 24 are formed by exposing the layer of material 20 to UV through a pattern mask. UV irradiation alters the titanium oxides in the areas of geometric physiologically functional features 24, thereby chemically altering the geometric physiologically functional features 24 relative to the surrounding surface area 22 of layer of material 20. The shape of geometric physiologically functional features can be circular, square, rectangle, triangle, parallel lines, intersecting lines or any combination. Each of the geometric physiologically functional features is from about 1 nanometer to about 75 µm, and preferably from about 1 nanometer to about 50 µm in feature width 26, or feature diameter if the geometric physiologically functional feature is circular. The gap distance 28 between each component of the geometric physiologically functional features may be less than, about equal to or greater than the feature width 26.

Figure 4:
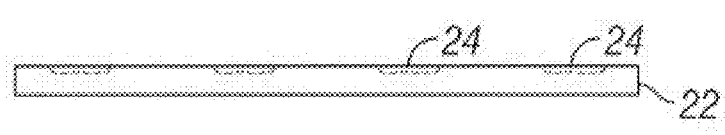
FIG. 4 is a cross-sectional view of FIG. 3 along line 4-4.

FIG. 4 is a cross-sectional view of FIG. 3 along line 4-4. The described geometric physiologically functional features 24 are indicated by the dotted lines, which indicate that the geometric physiologically functional features 24 are at the same level of the surrounding surface 22.

Figure 5A:
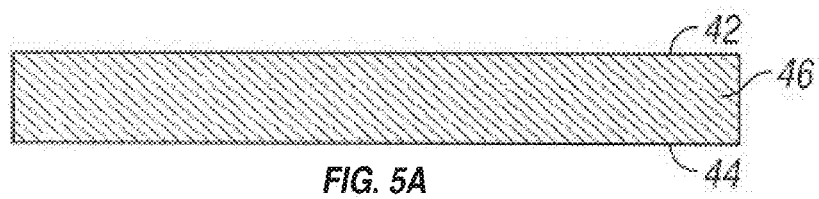
FIGS. 5A-5D are cross-sectional diagrammatic views of an embodiment, the combination of a-d representing the steps to make an inventive implantable material with elevated geometric physiologically functional features.

Referring to FIG. 5A, a portion of an implantable material 46 with surface 42 and 44 is shown.

Figure 5B:
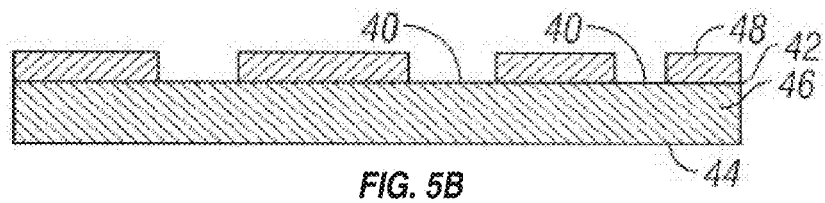

Referring to FIG. 5B, a machined mask 48 having laser-cut holes 40 of defined size ranging from about 1 nm to about 75 µm, and preferably from about 1 nm to 50 µm, patterned throughout coats at least one surface 42 of the implantable material 46 and is tightly adhered to the covered surface 42.

Figure 5C:
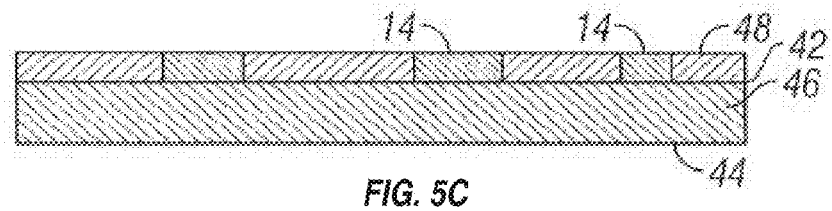

Referring to FIG. 5C, a thin film of material 30 was deposited into the space as defined by the holes 40, as seen in FIG. 5B, in the mask 48 by thin film deposition procedures.

Figure 5D:
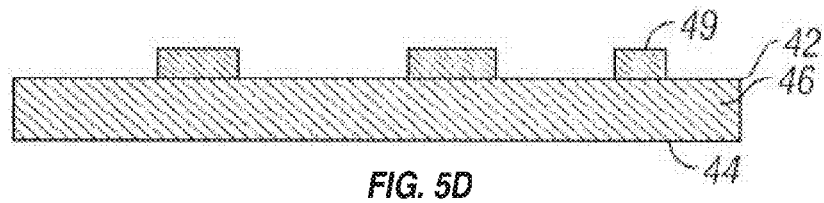

Referring to FIG. 5D, after deposition, the mask is removed to reveal the geometric physiologically functional features 49 patterned across the at least one surface 42 of the implantable material 46.

As described above, the shape of the holes in the mask could be in any of the shapes described for the geometric physiologically functional features including: circle, square, rectangle, triangle, parallel lines and intersecting lines, or any combination thereof. In the thin film deposition embodiment of the manufacturing the geometric physiologically functional features, the geometric physiologically functional features are elevated from the surface of the implantable material. The thickness of the geometric physiologically functional features is based upon the thickness of the holes in the mask, the thickness ranging from about 1 nm to about 20 micrometers. Preferably, the thickness of the holes in the mask range from about 1 nm to about 3 micrometers.

Figure 7A:
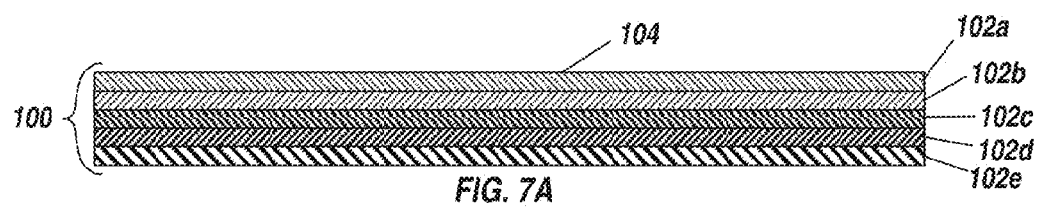
FIGS. 7A-7B are cross-sectional diagrammatic views of one embodiment.

The variations of geometric physiologically functional features may be added to a surface of an implantable biocompatible material by vacuum depositing a layer or layers of biocompatible material on the surface. In one embodiment, the geometry of the layer or layers of deposited material defines the geometric physiologically functional features. For example, an implantable material 100 has a surface 104, as illustrated in FIG. 7A. In one embodiment, the implantable biocompatible material may comprise one or more layers 102 of vacuum deposited material formed into a self-supporting structure, as illustrated by FIG. 7A showing a first layer 102a, a second layer 102b, a third layer 102c, a fourth layer 102d, and a fifth layer 102e. In another embodiment, the implantable biocompatible material includes a bulk material, either a bulk material alone or a bulk material covered by the one or more layers 102a-102e of vacuum deposited biocompatible material. Five layers 102a-102e of vacuum deposited material are illustrated; however, any number of layers may be included as desired or appropriate.

The one or more layers 102, may have thicknesses that are the same or different as desired or appropriate. Each layer may have a thickness in a range from about 1 nanometer to about 20 micrometers, from about 1 nanometer to about 10 micrometers, from about 1 nanometer to about 5 micrometers, or from about 1 nanometer to about 3 micrometers. Alternating layers 102 of varying thicknesses may be applied as to accommodate the geometric physiologically functional features.

In this embodiment, the geometric physiologically functional features may be added to the surface 104 by adding one or more layers 102 of vacuum deposited material. For example, referring to FIGS. 7B-7E, in one process, a mask 106 having holes 108 of defined size disposed therethrough and patterned throughout coats and is tightly adhered to at least a first portion of the surface 104. The holes 108 may be cut through the mask 106, for example, by using a laser or other method for forming holes through a material as known in the art, or the mask 106 may be fabricated including the holes 108 as may be known in the art. The thickness of the holes 108 may range about 1 nanometer to about 20 micrometers, from about 1 nanometer to about 10 micrometers, from about 1 nanometer to about 5 micrometers, or from about 1 nanometer to about 3 micrometers.

Figure 7B:
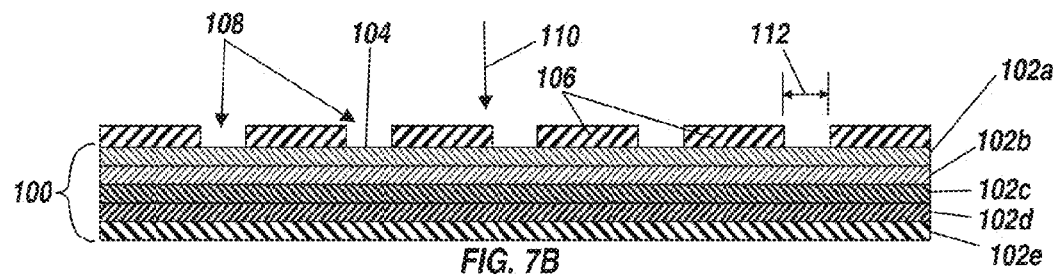
Figure 7C:
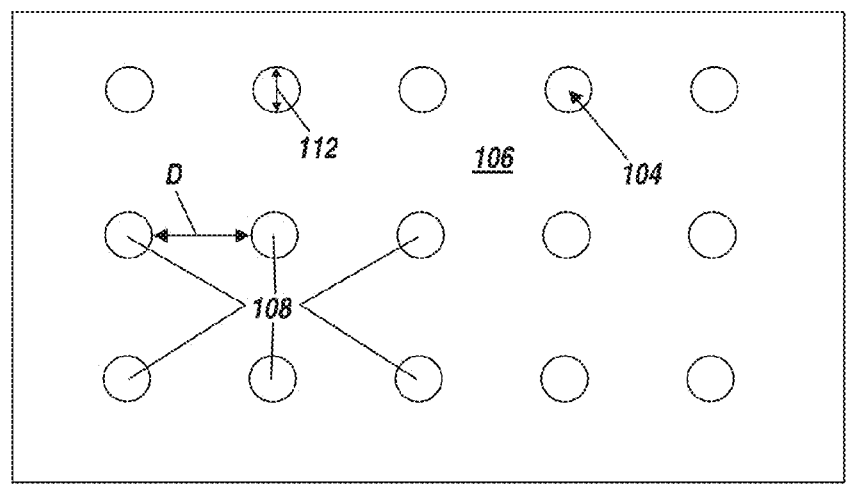
FIG. 7C is a top view of one embodiment.

The shape of the holes 108 as seen in FIG. 7C or as looking in the direction of arrow 110 in FIG. 7B may be any of the shapes described for the geometric physiologically functional features including: circle, square, rectangle, triangle, polygonal, hexagonal, octagonal, elliptical, parallel lines and intersecting lines, or any combination thereof. The holes 108 may have a width 112, or diameter 112 if the holes are circular, in a range between about 1 nanometer and about 75 micrometers, between about 1 nanometer and about 50 micrometers, between about 1 nanometer and about 2000 nanometers, or between about 1 nanometer and about 200 nanometers. Adjacent holes 108 may be spaced apart by a distance D in a range from about 1 nanometer to about 20 micrometers, from about 1 nanometer to about 10 micrometers, from about 1 nanometer to about 5 micrometers, or from about 1 nanometer to about 3 micrometers. The distance D may be less than, about equal to or greater than the width 112. In another embodiment (not shown), the width 112 of each of the holes 108 and/or the distance D between adjacent holes 108 may vary in size to form a patterned array of the holes 108.

Figure 7D:
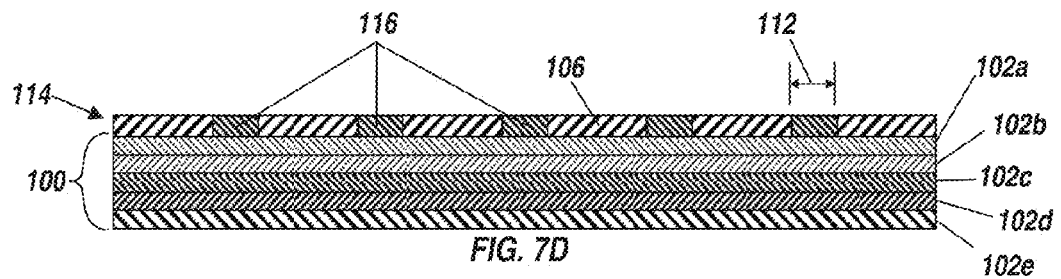
FIGS. 7D-7E are cross-sectional diagrammatic views of one embodiment of making the implantable material.
Figure 7E:
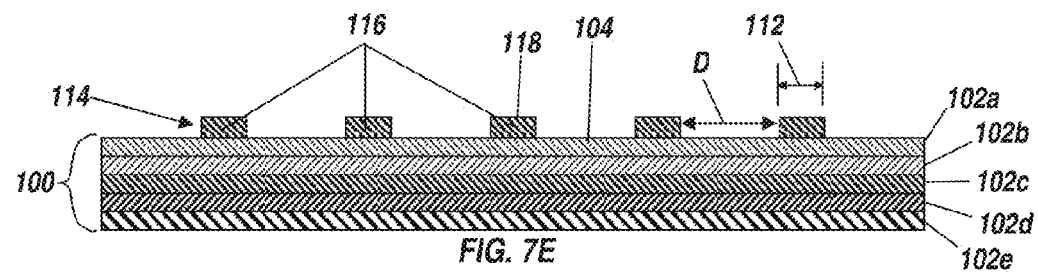

Referring to FIG. 7D, a layer 114 of material was deposited into a space as defined by the holes 108 in the mask 106 by vacuum deposition. The layer 114 has a thickness essentially the same as that of the mask 106. In some embodiments, the thickness of the mask may be variable across the mask 106. After removal of the mask 106, as shown in FIG. 7E, geometric physiologically functional features 116 are revealed patterned across the surface 104 of the implantable material 100. Each of the geometric physiologically functional features 116 includes a top surface 118. Each of the geometric physiologically functional features 116 has dimensions as described hereinabove for the holes 108 in the mask 106.

In another embodiment where geometry of the layer or layers of deposited material defines the geometric physiologically functional features, a patterned array of recesses may be formed each having a hydrophobic, hydrophilic or surface energy difference relative to the surface into which the recesses are added, meaning a top most surface of the deposited layers, the difference enhancing the binding, proliferation and migration of endothelial cells to and between the recesses and across the surfaces, recessed and top most. The hydrophobic, hydrophilic or surface energy differences relative to the surface may be formed, by way of example, any of the methods disclosed in commonly assigned U.S. patent application Ser. No. 12/428,981, filed Apr. 23, 2009, incorporated by reference herein.

In this embodiment, the recesses may be formed by a relative lack of deposition of a layer or layers onto a surface, or by machining recesses through a layer or layers of material vacuum deposited on a surface. For example, to produce a pattern of recesses similar to the pattern of geometric physiologically functional features 116 illustrated in FIG. 7E, in one example, a process begins by executing the steps described hereinabove with regard to FIGS. 7A-7E, to produce the pattern of geometric physiologically functional features 116 illustrated in FIG. 7E, except in this embodiment, the layer 114 of material is a sacrificial layer of material that is removed in a subsequent step.

Figure 8A:
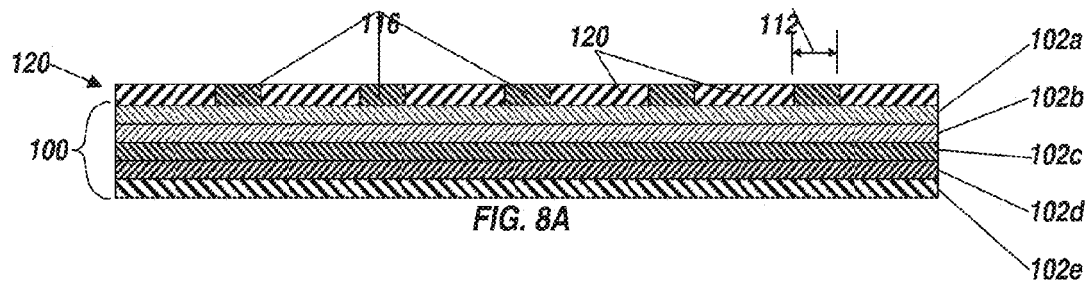
FIGS. 8A-8D are cross-sectional diagrammatic views of one embodiment.
Figure 8B:
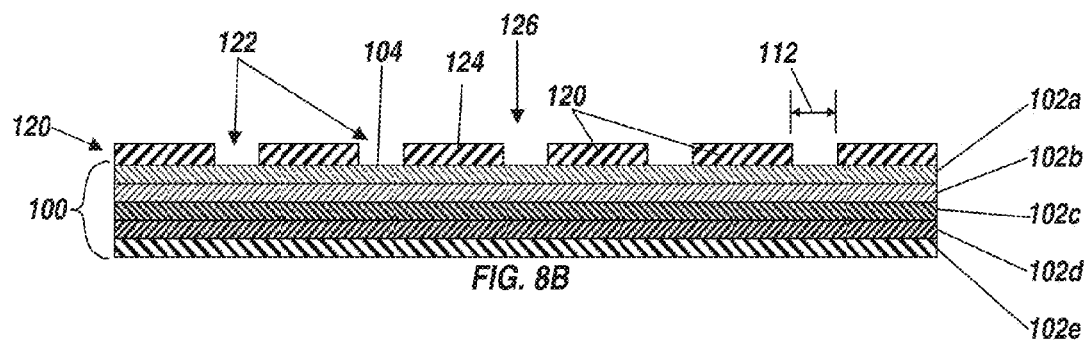

Referring to FIGS. 8A and 8B, a layer 120 of material is deposited into spaces between the geometric physiologically functional features 116 by vacuum deposition. The layer 120 has a thickness essentially the same as that of the geometric physiologically functional features 116. In this embodiment, after vacuum deposition of the layer 120, the geometric physiologically functional features 116 of the sacrificial layer 114 are removed, for example, by chemical etching or other method known in the art to reveal geometric physiologically functional features 122 patterned across the surface 104 of the implantable material 100. Each of the geometric physiologically functional features 122 is a recess that has a thickness or depth between a surface 124 of the layer 120 and the surface 104.

The shape of the recesses 122 as seen looking in the direction of arrow 126 in FIG. 8B may be any of the shapes described for the geometric physiologically functional features including: circle, square, rectangle, triangle, polygonal, hexagonal, octagonal, elliptical, parallel lines and intersecting lines, or any combination thereof. The recesses 122 may have the width 112, or diameter if the recesses 122 are circular, in a range between about 1 nanometer and about 75 micrometers, alternatively between about 1 nanometer and about 50 micrometers, alternatively between about 1 nanometer and about 2000 nanometers, or alternatively between about 1 nanometer and about 200 nanometers. Adjacent recesses 122 may be spaced apart by the distance D in a range from about 1 nanometer to about 20 micrometers, from about 1 nanometer to about 10 micrometers, from about 1 nanometer to about 5 micrometers, or from about 1 nanometer to about 3 micrometers. The distance D may be less than, about equal to or greater than the width 112. In another embodiment (not shown), the width 112 of each of the recesses 122 and/or the distance D between adjacent recesses 122 may vary in size to form a patterned array of the recesses 122.

Figure 9A:
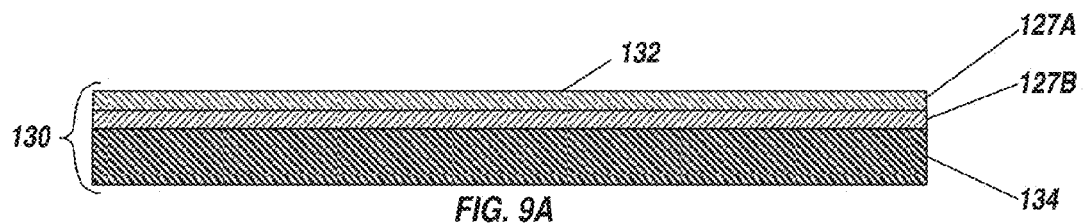
FIGS. 9A-9B are cross-sectional diagrammatic views of one embodiment.

In another embodiment, the recesses 122 having width and spacing as described hereinabove with regard to FIGS. 8A and 8B may be formed by machining the recesses 122 through a layer or layers 127 of vacuum deposited material. For example, an implantable material 130 having a surface 132, may comprise a bulk material 134, and the one or more layers 127 of vacuum deposited material, as illustrated in FIG. 9A.

Figure 8C:
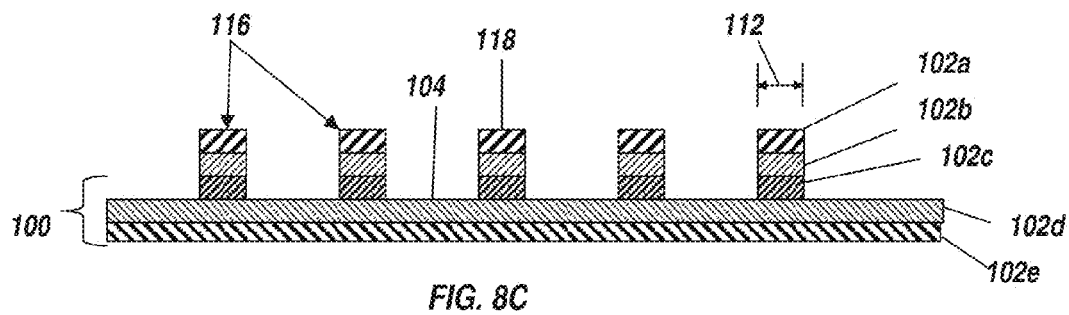

Alternatively, as shown in FIG. 8C, the geometric physiologically functional features 116 themselves include a plurality of deposited layers, wherein the geometric physiologically functional features 116 include the first layer 102a, the second layer 102b, and the third layer 102c. The geometric physiologically functional features 116 are deposited through a mask as previously indicated, on top of structural material of the stent or other medical device include deposited layer 102d and 102e. Alternatively, the geometric physiologically functional features 116 include the first layer 102a and the second layer 102b, deposited through the mask whereby the structural material of the stent or other medical device includes the layers 102c-102d. Alternatively, the geometric physiologically functional features 116 include the first layer 102a, the second layer 102b, the third layer 102c, and the fourth layer 102d, whereby the structural material of the stent or other medical device includes the fifth layer 102e. When additional layers 102a-102d are included in the geometric physiologically functional feature 116, the thickness of the layers as deposited can be modified to be a narrower or decreased thickness as to allow for the geometric physiologically functional feature 116 to be adjusted to a particular thickness. The layers of different vacuum deposited materials can be deposited to create the elevated surfaces having inherently different material properties. Alternatively, layers of the same vacuum deposited material can be deposited having differences in grain size, grain phase, and/or surface topography or variations of hydrophobic, hydrophilic or surface energy difference relative to the surface of the stent or structural material.

Figure 8D:
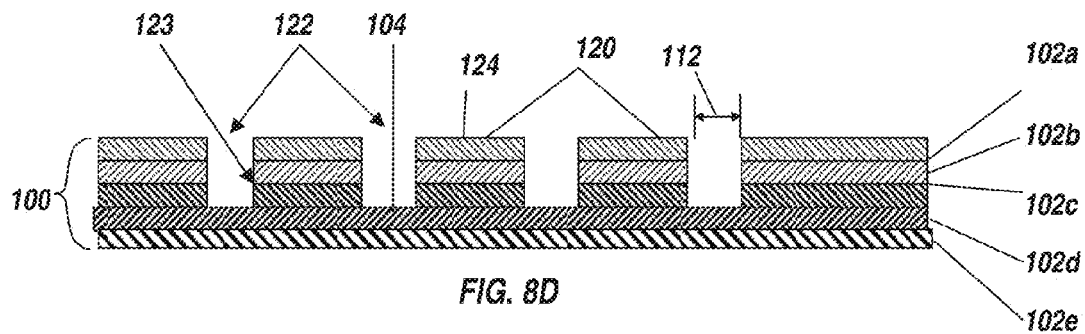

Alternatively, as shown in FIG. 8D, the recesses 122 may include a plurality of layers 102 to provide for differences in grain size, grain phase, and/or surface topography or variations of hydrophobic, hydrophilic or surface energy difference relative to the surface of the stent or structural material. The recesses 122 may be formed by the surface 124 being deposited through a mask as to form the layer 120 that gives rise to the plurality of recesses 122 with a wall 123. As such, the recesses 122 include an inner wall 123 including the first layer 102a, the second layer 102b, and the third layer 102c, whereby the surface 104 is on layer 102d, which is exposed on the bottom of the recess 122 and surface 124 is on top of layer 102a. Alternatively, the recesses 122 may include a wall of the first layer 102a and the second layer 102b, whereby the surfaces 124 are deposited through a mask, and the structural material of the stent or other medical device includes the layers 102d-102e. Alternatively, the recesses 122 include a wall of the first layer 102a, the second layer 102b, the third layer 102c, and the fourth layer 102d, and surfaces 124 are deposited through a mask whereby surface 102e that acts as the surface 104 of the structural material of the medical device. When additional layers 102a-102d are included as the wall in the geometric physiologically functional feature 116, the thickness of the layers as deposited can be modified to be a narrower or decreased thickness as to allow for the geometric physiologically functional feature 116 to be adjusted to a particular thickness. The layers of different vacuum deposited materials can be deposited to create recesses having inherently different material properties. Alternatively, layers of the same vacuum deposited material can be deposited having differences in grain size, grain phase, and/or surface topography or variations of hydrophobic, hydrophilic or surface energy difference relative to the surface of the stent or structural material.

Figure 9B:
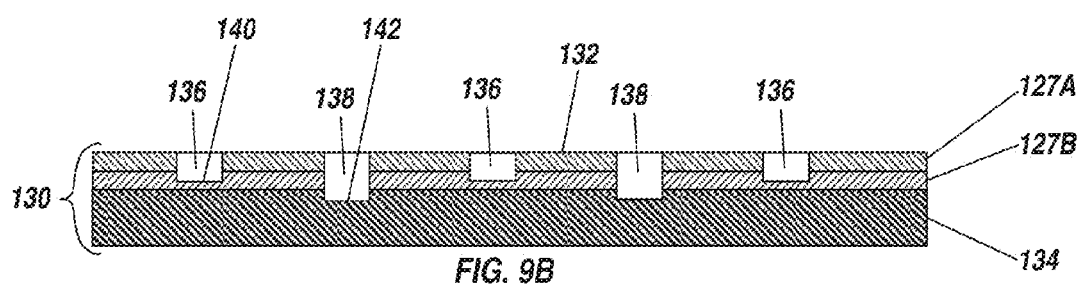

Referring to FIG. 9B, recesses 136 may be machined into the surface 132 of the implantable material 130 to have a depth greater than a thickness of a first layer of material 127a or recesses 138 may be machined into the surface 132 of the implantable material 130 to have a depth greater than a thickness of the first and second layers 127a, 127b of material. Two layers are illustrated for convenience of explanation and illustration; however, any number of layers 127 of material may be used as desired or appropriate. In this aspect, each of the recesses 136 has a thickness or depth between the surface 132 of the layer 127 and a surface 140 that is within a second layer 127b. Similarly, each of the recesses 138 has a thickness or depth between the surface 132 of the layer 127a and a surface 142 that is within the bulk material 134.

An implantable material including geometric physiologically functional features comprising a layer or layers of vacuum deposited material, as illustrated by the geometric physiologically functional features 116 in FIG. 7E, recesses disposed through one or more layers of vacuum deposited material, as illustrated by the recesses 122 in FIG. 8B or the recesses 136 or 138 in FIG. 9B, has an inherently different structure than a block of material having recesses cut into it. The reason for this inherent difference lies in the differences in the materials making up surfaces exposed by the recesses. For example, in the case of a block of material and assuming that the block material is uniform in regard to material properties, an undisturbed surface of the block and a surface within a recess or groove cut into the block have the same material properties.

In contrast, layers of different vacuum deposited materials can be deposited to create recessed and/or elevated surfaces having inherently different material properties. In fact, layers of the same vacuum deposited material can be deposited having differences in grain size, grain phase, and/or surface topography. The alternative grain size, grain phase, and/or surface topography may be included or formed, by way of example, any of the methods disclosed in commonly assigned U.S. patent application Ser. No. 12/428,981, filed Apr. 23, 2009, incorporated by reference herein. For example, surfaces of the recesses 122, 136 can be deposited to have a roughened surface topography and a large grain size and surfaces of the material deposited defining the recesses 122, 136, for example the layer 120 illustrated in FIG. 8B, can have a relatively smoother surface topography and/or a smaller grain size.

In addition to utilization of the above described geometric physiologically functional features, endothelial migration may be further promoted by geometrically tailored leading and trailing edge surfaces of structural members of the implantable device and/or by the addition of surface structural features thereto. For example, referring to FIG. 10, an artery 200 is illustrated having an arterial wall 202. An implantable medical device, for example, a stent 204 is illustrated being disposed within the artery 200 in engagement with the arterial wall 202. The stent 204 may include a plurality of structural members 206 that are interconnected. As evident from the cross-sectional view illustrated in FIG. 10, correct placement of the structural members 206 relative to the arterial wall 202 results in a plurality of tissue mounds 208 protruding between the structural members 206.

Figure 10:
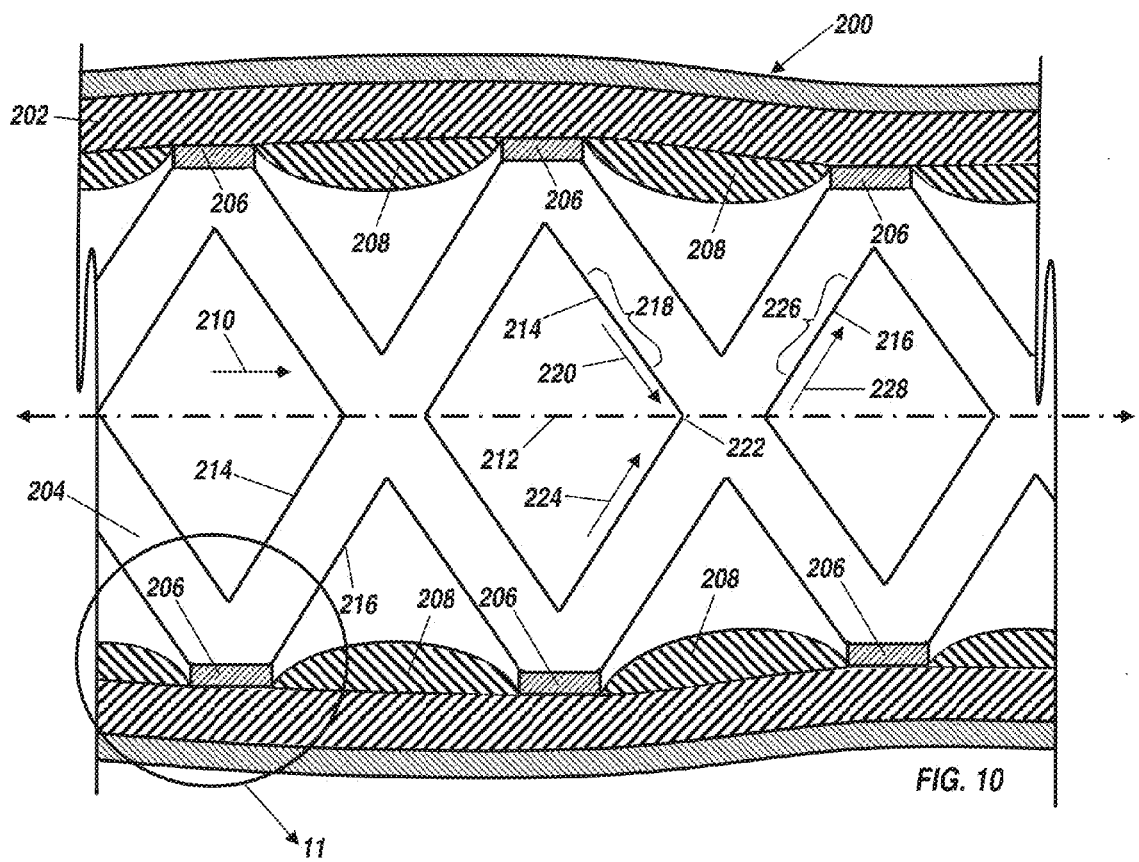
FIG. 10 is a cross-sectional view of an artery having an arterial wall including an implantable medical device.

FIG. 10 further illustrates an exemplary direction 210 of blood flow, which is generally parallel to a longitudinal axis 212 of the artery 200. Endothelial regeneration of the arterial wall 202 proceeds in a multicentric fashion following implantation of the structural members 206. However, due to stresses associated with the direction 210 of blood flow, the endothelial regeneration may include a preferred direction of migration. Further, individual structural members 206 may have distinct surface regions experiencing different types of stress depending on orientation of the individual structural members 206 relative to the direction 210 of blood flow.

Figure 11:
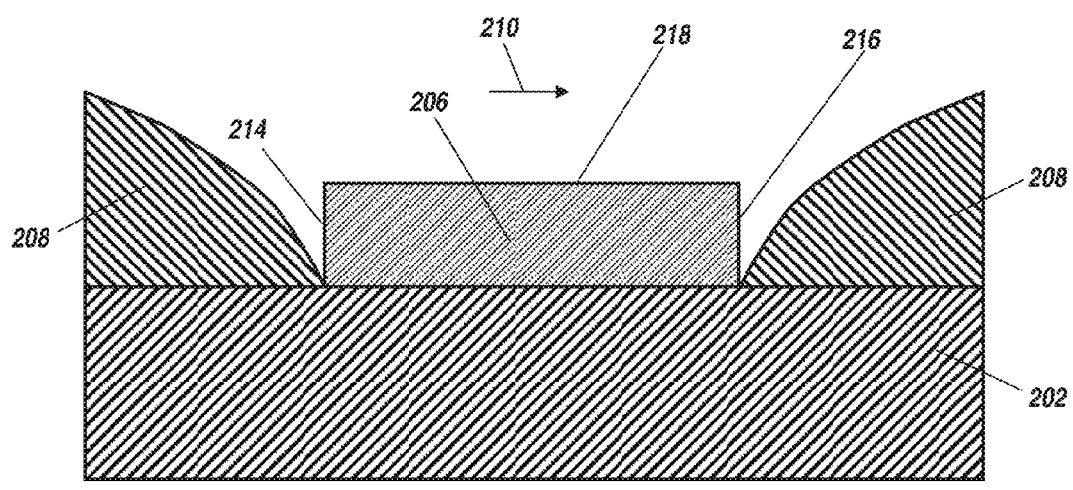
FIG. 11 is an enlarged cross-sectional view from circle 11 in FIG. 10 of the implantable medical device, in accordance with one embodiment.

Referring to FIGS. 10 and 11, as well as FIGS. 21A-B and FIGS. 22A-B the structural member 206 (circled in FIG. 10) includes a leading edge 214 relative to the direction of blood flow 210 and a trailing edge 216 relative to the direction of blood flow 210. The leading edge 214 is the first edge to experience or interact with the blood flow 210, while the trailing edge 216 subsequently interacts with the blood flow 210 after the blood flow 210 leaves the leading edge 214. Referring to FIG. 11, the structural member 206 may have a surface region 218 on the leading edge 214 that experiences shear stress due to the direction 210 of blood flow. Shear stress in fluids is the parallel or tangential force applied over the cross section of an area. This shear stress is dependent on the velocity of blood flow. The velocity of blood flow may range between about 0.05 to 0.2 m/s depending on the location of the stent, blood pressure, blood vessel flexibility, and the like.

The leading edge 214 of the structural member 206 may have a plurality of surface regions 218, 222 that are exposed to shear and/or normal stress associated with the direction 210 of the blood flow. For example, referring to FIG. 10, shear stress at surface region 218 is provided by a component 220 of blood flow along the leading edge 214. Increasing the angle measured between the leading edge 214 of the surface region 218 and the direction 210 of blood flow decreases the magnitude of the component 220 of blood flow, and therefore reduces the shear stress at the surface region 218. A leading edge that is oriented generally normal to blood flow may experience stress that is substantially normal having little or no shear component. For example, at surface region 222 illustrated in FIG. 10, the component 220 and component 224 of blood flow may cancel out leaving only a generally normal stress associated with the direction 210 of blood flow directed along the longitudinal axis 212.

Similarly, the trailing edge 216 of the structural member 206 may have a plurality of surface regions 226 that are exposed to shear and/or normal stress associated with the direction 210 of the blood flow. For example, referring to FIGS. 10, 21A and 22A shear stress at surface region 226 is provided by a component 228 of blood flow along the trailing edge 216. Increasing the angle measured between the trailing edge 216 of the surface region 226 and the direction 210 of blood flow decreases the magnitude of the component 228 of blood flow, and therefore reduces the shear stress at the surface region 226. A trailing edge that is oriented generally normal to blood flow (See FIG. 13A) may be in a low flow eddy region and may experience little or no stress associated with the direction 210 of blood flow directed along the longitudinal axis 212.

Figure 12A:
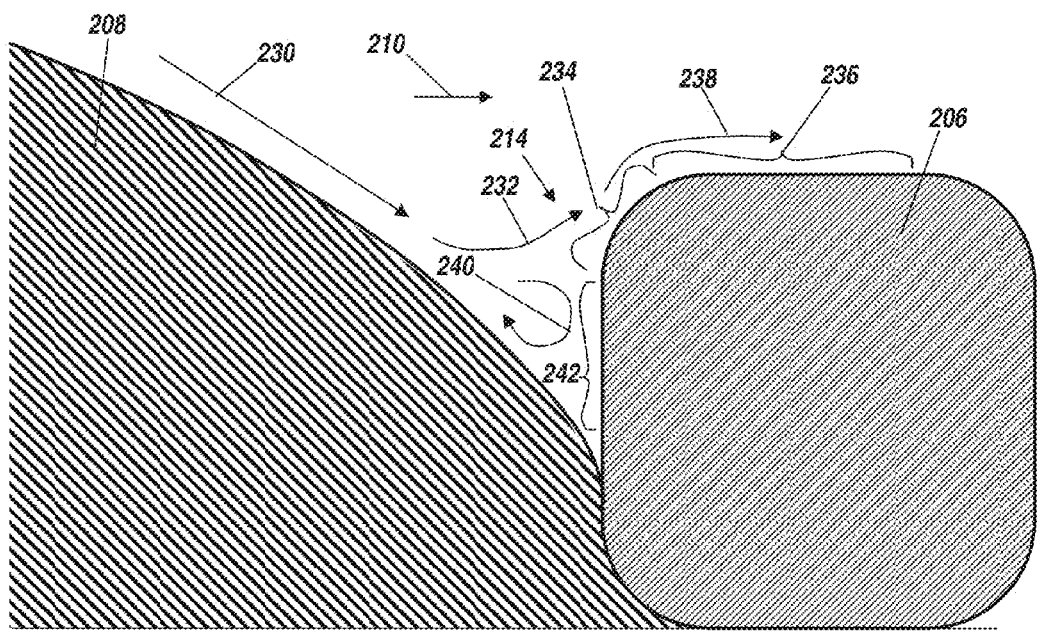
FIG. 12A is a cross-sectional view of one embodiment of the structural member having a generally rounded rectangular cross-section.
Figure 12B:
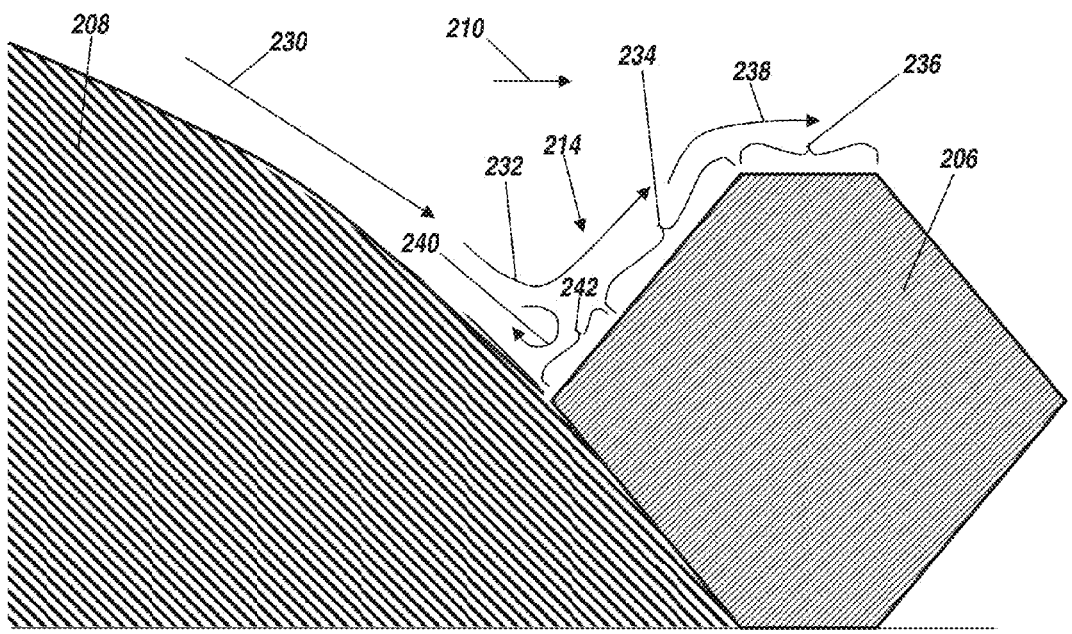
FIG. 12B is a cross-sectional view of one embodiment of the structural member having a generally hexagonal cross-section.

Referring to FIG. 12A, the leading edge 214 of the structural member 206 includes a generally rounded rectangular cross-section is illustrated oriented substantially normal to the direction 210 of blood flow. Referring to FIG. 12B, the leading edge 214 of the structural member 206 includes a generally hexagonal cross-section is illustrated oriented substantially normal to the direction 210 of blood flow. Referring to both FIGS. 12A and 12B and not being bound by theory, blood flows around the tissue mound 208 before reaching the leading edge 214, as illustrated by arrow 230. Proximate to the leading edge 214, blood is diverted around the structural member 206 as indicated by arrow 232 and flows over a upstream surface region 242, then a second surface region 234 of the leading edge 214, thereby causing a shear stress at the second surface region 234. The upstream surface region 242 is adjacent to the tissue mound 208, while the second surface region 234 is approximately at an angle between 0 and 180 degrees. Blood continues to flow over a third surface region 236 (which is contiguous with the surface 234) of the structural member 206, as illustrated by arrow 238, thereby causing a shear stress at the third surface region 236.

Note that a structural member having a generally rounded rectangular cross-section may result in formation of an eddy region as indicated by curved arrow 240 in FIG. 12A. The eddy region 240 represents a region of low flow and may be associated only weakly with normal and/or shear stress at the upstream surface region 242. Thus, in this geometry, EC migration over the upstream surface region 242 would not benefit from exposure to shear stress as would EC migration over the second and third surface regions 234, 236. Not wishing to be bound by theory, it is contemplated that EC migration from a source of EC to a surface region, such as from the tissue mound 208 to the third surface region 236, would be enhanced by a continuous shear stress applied from the tissue mound 208 to the third surface region 236. Such continuous shear stress is not evident in the geometry illustrated in FIG. 12A.

Referring now to FIG. 12B, the eddy region as indicated by curved arrow 240 may also be formed with this cross-sectional geometry; however, in this geometry the eddy region 240 is associated with a smaller upstream surface region 242 compared with the eddy region 240 illustrated in FIG. 12A. Thus, although the hexagonal cross-sectional geometry for the structural member 206 may be an improvement over the generally rounded rectangular cross-section illustrated in FIG. 12A, the upstream surface region 242 would not be exposed to shear stress. Thus, continuous shear stress from the tissue mound 208 to the third surface region 236 is not evident in the geometry illustrated in FIG. 12B.

Referring to FIGS. 12C-12D and 21A-21B, the leading edge 214 of the structural member 206 includes a modified cross-section is illustrated oriented substantially normal to the direction 210 of blood flow. A first edge 211 forms a first surface region 213. The first edge 211 joins the leading edge 214 adjacent to the tissue mound 208 to form the second surface region 234 including generally J-shaped cross-section or an elliptical, concave curvilinear, or circular cross-section to couple the blood flow from the tissue mound 208 and create shear stress at the second surface region 234. In this cross-sectional geometry, not wishing to be bound by theory, the blood flows around the tissue mound 208 before reaching the leading edge 214, as illustrated by arrow 230. Proximate to the leading edge 214, the blood flow is diverted around the structural member 206, as indicated by arrow 232, and flows over a second surface region 234 of the leading edge 214, thereby causing shear stress at the second surface region 234. Blood continues to flow over the third surface region 236 (which is contiguous with the surface 234) of the structural member 206, as illustrated by arrow 238, thereby causing a shear stress at the third surface region 236. Preferably, increased shear stress is about 15 dynes/cm2 caused by the blood flow from the second surface region to the third surface regions, whereby EC's will migrate roughly at a rate of 25 µm/hr or about 2.5 times the diameter of an EC, which is nominally 10 µm. Further such migration has been observed in the direction of the blood flow with little migration observed against the flow. Alternatively, the configuration of the second surface region 234 generates shear stress increased from normal blood flow, which is a pressure of about 1.5 dynes/cm2. As such, the configuration is optimized to increase the shear stress of the blood flow to be a pressure between about 5 and 25 dynes/cm2 at the third surface region 236.

Figure 12C:
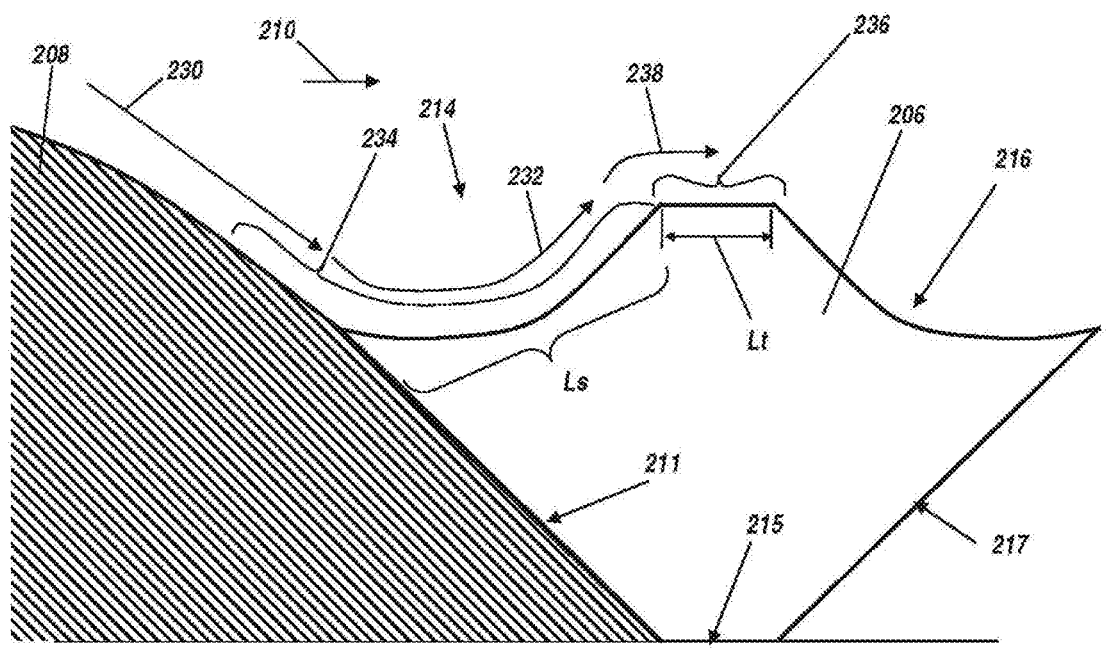
FIGS. 12C-12D are cross-sectional views of one embodiment of the structural member entirely lacking an eddy region.

Note that blood flow over the leading edge 214 of the structural member 206 having the modified cross-sectional geometry illustrated in FIG. 12C entirely lacks an eddy region. The structural member thus retains a general cross section in a generally, hexagonal, trapezoidal, polygonal, or an arrow-head configuration. In this geometry, blood flows over the tissue mound 208 and over the second surface region 234, which is contiguous between the tissue mound 208 and the third surface region 236. Such blood flow provides shear stress to the tissue mound 208 and the second surface region 234 contiguously. Thus, in this geometry, EC migration benefits from continuous exposure to shear stress from the tissue mound 208 to the third surface region 236. In one embodiment, the trailing edge 216 is symmetrical with the leading edge 214 and includes a modified cross-section is illustrated oriented substantially normal to the direction 210 of blood flow to include a generally J-shaped cross-section or an elliptical, concave curvilinear, or circular cross-section to couple the blood flow. The trailing edge 216 may include a radius curvature similar to that of the leading edge 214 and the second surface region 234. Preferably, the trailing edge 216 includes a surface region as to enforce the shear stress on the third surface region and maintain the shear stress on the trailing edge's 216 surface region. Alternatively, the trailing edge 216 may be asymmetrical.

Figure 12D:
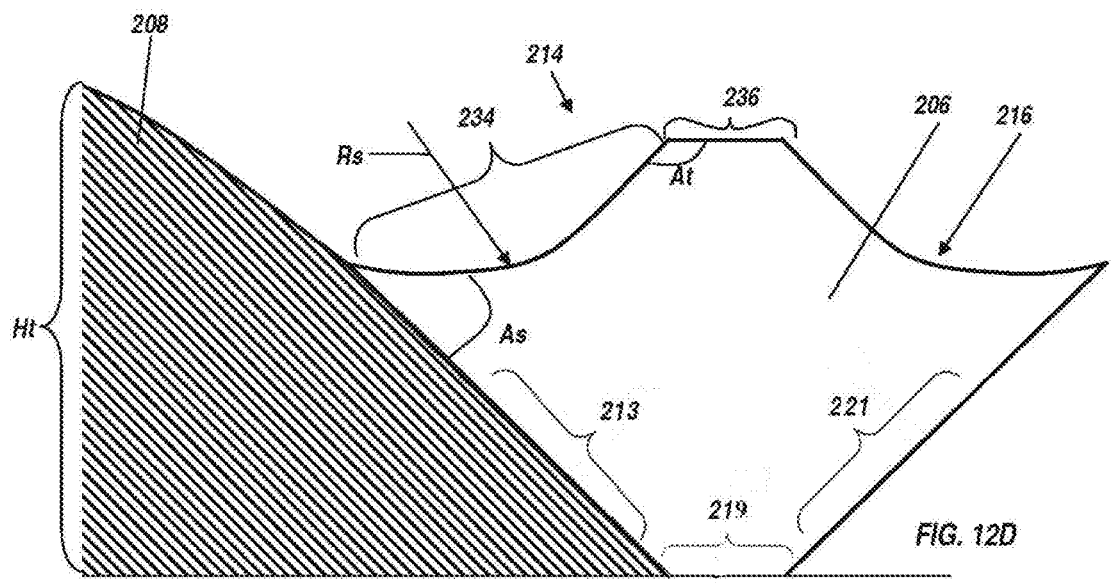

As shown in FIG. 12D, the second surface region 234 includes a radius of curvature Rs. Preferably, the radius of curvature Rs is the reciprocal of a radius approximately 1/Rs, where Rs is between about 1 µm to about 75 mm, alternatively from about 1 nm to about 50 mm, alternatively from about 1 nm to about 2000 µm, and preferably from about 1 nm to about 200 mm. The radius curvature Rs of the second surface region 234 may be selected for the particular tissue mound 208 that might be adjacent to the structural member 206. For example, the radius of curvature Rs may be selected to be greater where the tissue mound 208 is found to grow at a height Ht greater than the height, thickness or width of the structural member 206. Such a tissue mound 208 with a height Ht greater the height or thickness of the structure member 206 would require a greater degree of curvature to retain a contiguous blood flow from the tissue mound 208 over the second surface region 234 and to the third surface region 236, as to provide shear stress to the tissue mound 208 for continual EC migration over such regions. Preferably, the height of the second surface region 234 is above the height of the connecting points of the leading edge 214 and the first edge 211 and above the height of the connecting points of the trailing edge 216 and the third edge 216. The differential in the height of the second surface region 234 may also provide for the continuous shear stress from the second surface region 234 to the third surface region 236.

As shown in FIG. 12D, the leading edge 214 of the second surface region 234 combines with the first edge 211 to form an angle As. Preferably, angle As is less than 90 degrees, alternatively, between about 1 and 80 degrees, alternatively, between about 10 and 75 degrees, alternatively, between about 20 and 60 degrees. The angle As is generally acute, such as to provide the tissue mound 208 to grow into the first edge 211 on about a generally angular or sloped configuration. The second surface region 234 connects to the third surface region 236 to form an angle At. Preferably, angle At is greater than 90 degrees, alternatively, between about 90 and 179 degrees, alternatively, between about 100 and 160 degrees, alternatively, between about 120 and 140 degrees.

The angle At is generally obtuse, such as to provide the contiguous shear stress 238 from the surface 234 of the structural member 206 to the third surface region 236. In one embodiment, the length Lt of the third surface region 236 is less than the length Ls of the second surface region 234, as to maintain the contiguous shear stress over the third surface region 236. Length Ls and length Lt may be between about 1 µm to about 75 mm, alternatively from about 1 nm to about 50 mm, alternatively from about 1 nm to about 2000 µm, and preferably from about 1 nm to about 200 mm. Preferably, the strut thickness is below 250 µm for proper endothelialization.

In one embodiment, the first edge 211 joins the second edge 215; whereby the second edge 215 joins a third edge 217, as shown in FIGS. 12C-12D. The third edge 217 joins the trailing edge 216 to form the substantially hexagonal cross-sectional configuration. In this embodiment, the second edge forms a sixth surface 219, and the third edge 217 forms a fifth surface 221. While a hexagonal configuration is shown, alternative polygonal configuration may be utilized that maintain the geometry for blood flows over the tissue mound 208 and over the second surface region 234 to be contiguous between the tissue mound 208 and the third surface region 236 and to provide for shear stress to the tissue mound 208 and the second surface region 234 contiguously. In one embodiment, the first edge 211 joins the second edge 215 at a generally obtuse angle, preferably, greater than 90 degrees, alternatively, between about 90 and 179 degrees, alternatively, between about 100 and 160 degrees, alternatively, between about 120 and 140 degrees. In one embodiment, the second edge 215 joins the third edge 217 at a generally obtuse angle, preferably, greater than 90 degrees, alternatively, between about 90 and 179 degrees, alternatively, between about 100 and 160 degrees, alternatively, between about 120 and 140 degrees.

Figure 13A:
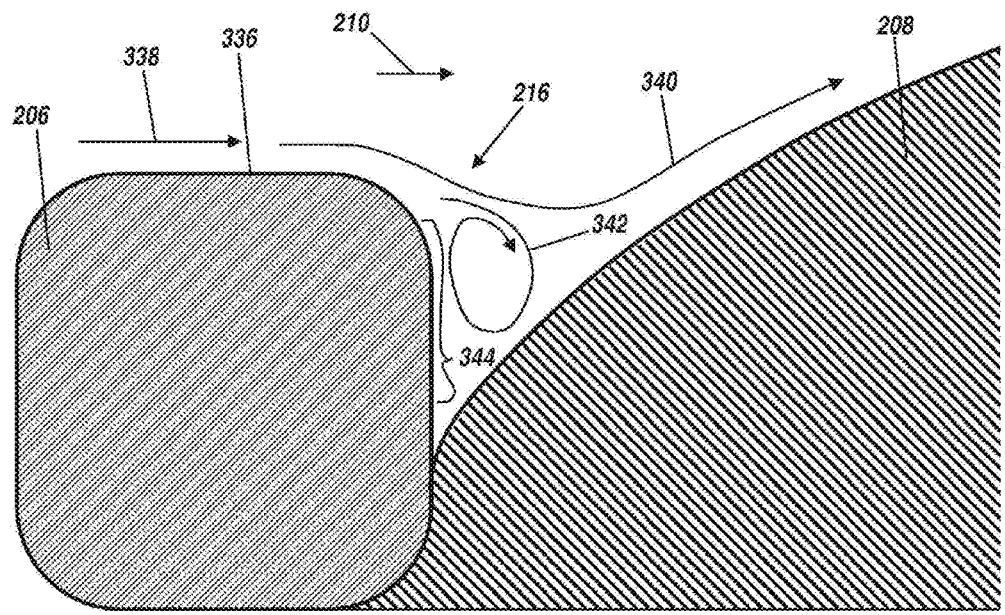
FIG. 13A is a cross-sectional view of one embodiment of the trailing edge of a structural member having a generally rounded rectangular cross-section.

Referring to FIG. 13A, the trailing edge 216 of the structural member 206 including a generally rounded rectangular cross-section is illustrated in one embodiment oriented substantially normal to the direction 210 of blood flow. Not wishing to be bound by theory, the blood flows 340 over a third surface region 236 of the structural member 206, as illustrated by arrow 338, thereby causing a shear stress at the surface region 236. In one embodiment, the surface region is substantially perpendicular to the longitudinal axis of the structural member 206. The blood flows 340 over the trailing edge 216 and continues past the tissue mound 208, as illustrated by arrow 340. An eddy region, as represented by arrow 342, is formed in the wake of the structural member 206 between the tissue mound 208. The eddy region 342 represents a region of low flow and may be associated only weakly with normal and/or shear stress at a downstream surface region 344 bound by the structural member and vessel, which is substantially perpendicular to the surface region 236. Thus, in this geometry, EC migration over the downstream surface region 344 would not benefit from exposure to shear stress as would EC migration over the third surface region 236. Not wishing to be bound by theory, the EC migration over a surface region, such as the distal surface region 344, would be enhanced by shear stress resulting from the flow of blood thereover. Such shear stress is not evident for the surface region 344 in the geometry illustrated in FIG. 13A.

Figure 13B:
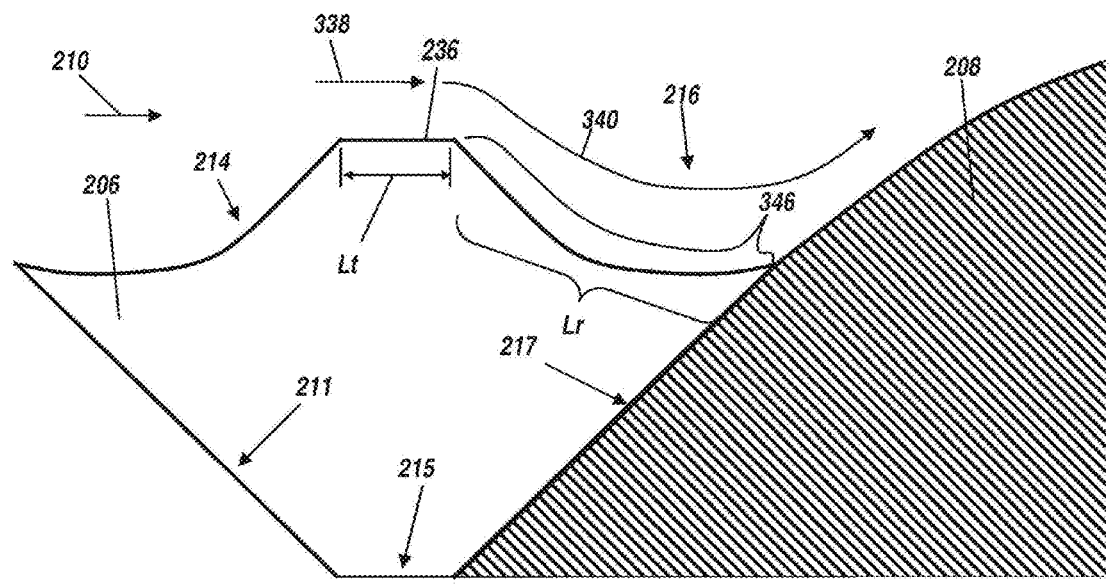
FIGS. 13B-13C are cross-sectional views of one embodiment of the trailing edge of the structural member 206 having a modified cross-section.

Referring to FIG. 13B, one embodiment of the trailing edge 216 of the structural member 206 having a modified cross-section is illustrated oriented substantially normal to the direction 210 of blood flow 340. Not wishing to be bound by theory, blood flows over the third surface region 236 of the structural member 206, as illustrated by the arrow 338, thereby causing a shear stress at the third surface region 236. The third surface region 236 is substantially perpendicular to the longitudinal axis of the structural member 206. Blood flows over the trailing edge 216 and continues past the tissue mound 208, as illustrated by arrow 340. In this embodiment, the trailing edge 216 includes a curvilinear or elliptical cross-section to form a fourth surface region 346, which is curvilinear or elliptical relative to the tissue mound 208. Note that blood flow 340 over the trailing edge 216 of the structural member 206 having the modified cross-sectional geometry illustrated in FIG. 13B and entirely lacks an eddy region. Thus, in this geometry, the blood flows over the fourth surface region 346 of the trailing edge 216. EC migration over the fourth surface region 346 thereby benefits from exposure to shear stress as would EC migration over the surface region 236. Not wishing to be bound by theory, the EC migration over the fourth surface region 346 would be enhanced by shear stress resulting from the flow of blood 340 thereover.

Figure 13C:
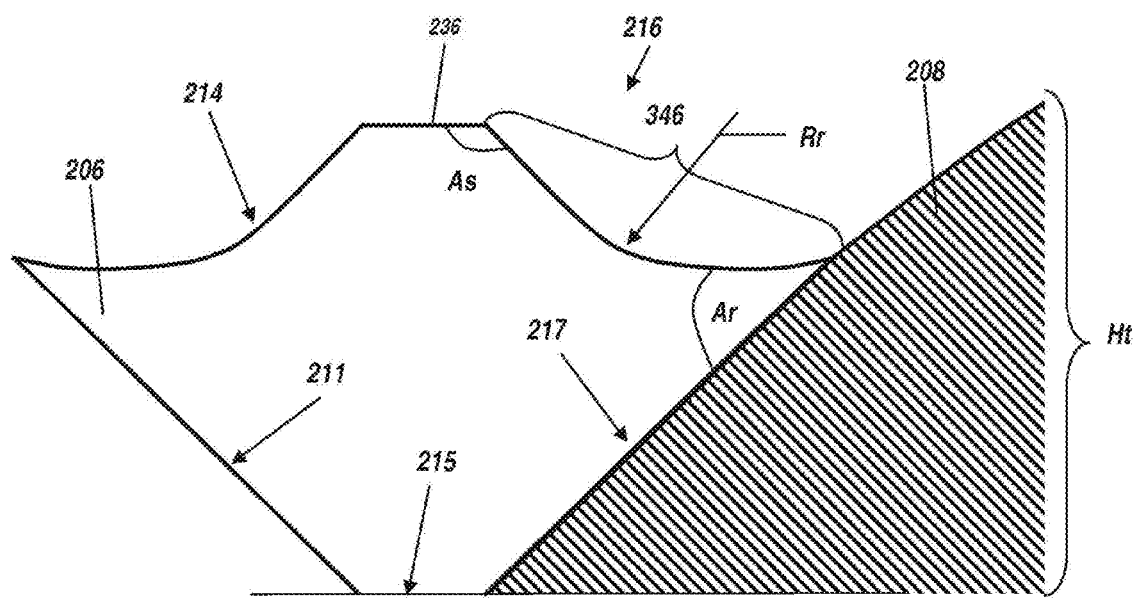

As shown in FIG. 13C, the fourth surface region 346 includes a radius of curvature Rr. Preferably, the radius of curvature Rr is the reciprocal of a radius approximately 1/Rr, where Rr is between about 1 nm to about 75 μm, from about 1 μm to about 75 mm, alternatively from about 1 nm to about 50 mm, alternatively from about 1 nm to about 2000 μm, and preferably from about 1 nm to about 200 mm. Preferably, the radius of curvature maintains the thickness of the structural member below 250 μm as to maintain endothelialization. The radius curvature Rr of the fourth surface region 346 may be selected for the particular tissue mound 208 that might be adjacent to the structural member 206. For example, the radius of curvature Rr may be selected to be greater where the tissue mound 208 is found to grow at a height Ht greater than the height, thickness or width of the structural member 206. Such a tissue mound 208 with a height Ht greater the height or thickness of the structure member 206 would require a greater degree of curvature to retain a contiguous blood flow from the tissue mound 208 over the third surface region 236 and to the fourth surface region 346, as to provide shear stress to the tissue mound for continual EC migration over such regions. Preferably, the height of the second surface region 236 is above the height of the connecting points of the leading edge 214 and the first edge 211 and above the height of the connecting points of the trailing edge 216 and the third edge 217. The differential in the height of the second surface region 234 may also provide for the continuous shear stress from the second surface region 234 to the fourth surface region 346.

As shown in FIG. 13C, the trailing edge 216 of the fourth surface region 346 combines with the third edge 217 to form an angle Ar. Preferably, angle Ar is less than 90 degrees, alternatively, between about 1 and 80 degrees, alternatively, between about 10 and 75 degrees, alternatively, between about 20 and 60 degrees. The angle Ar is generally acute, such as to provide the tissue mound 208 to grow into the third edge 217 on about a generally angular or sloped configuration. The third surface region 336 236 connects to the fourth surface region 346 to form an angle Aq. Preferably, angle Aq is greater than 90 degrees, alternatively, between about 90 and 179 degrees, alternatively, between about 100 and 160 degrees, alternatively, between about 120 and 140 degrees. The angle Aq is generally obtuse, such as to provide the contiguous shear stress 340 from the surface 336 236 of the structural member 206 to the fourth surface region 346. In one embodiment, the length Lt of the third surface region 336 236 is less than the length Lr of the fourth surface region 346, as to maintain the contiguous shear stress over the fourth surface region 346, as shown in FIG. 13B.

In one embodiment, the third edge 217 joins the second edge 215, whereby the second edge 215 joins the first edge 211, as shown in FIGS. 13B-13C. The first edge 211 joins the leading edge 214 to form the substantially hexagonal cross-sectional configuration. While a hexagonal configuration is shown, alternative polygonal configurations may be utilized that maintain the geometry for blood flows over the third surface region 336 236 and be contiguous between the fourth surface region 346 and the tissue mound 208 and to provide for shear stress to the tissue mound 208 and the second surface region 234 contiguously Instead of or in addition to geometrically tailored leading and trailing edge surfaces of the structural members 206, as described hereinabove with regard to FIGS. 12A-13C, endothelial migration across an implantable device may be promoted by the addition grooves to surfaces of the implantable device. When a groove is disposed, or provided, on, or in, a surface of an intravascular stent, the rate of migration of endothelial cells upon the surface may be increased over that rate of migration which would be obtained if the surface were not provided with the groove. Further, EC within a groove oriented with blood flow experience shear stress of the blood flow directly and would therefore be expected to migrate in the direction of the blood flow as described hereinabove. The formation of the grooves may be achieved by the methods in commonly assigned U.S. patent application Ser. No. 09/861,219, filed May 10, 2001 and Ser. No. 13/099,980, filed May 3, 2011, both incorporated by reference herein.

Figure 14A:
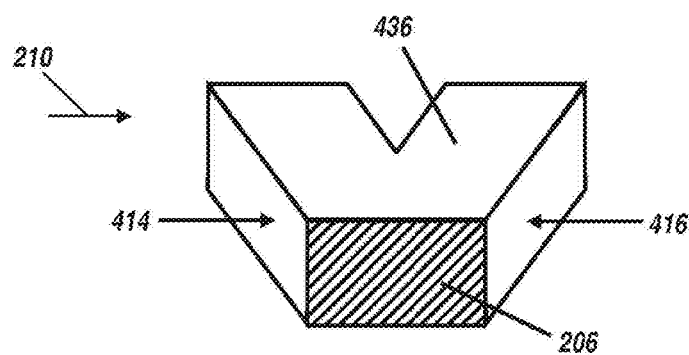
FIG. 14A is a perspective view of one embodiment of the structural member including a luminal surface, a leading edge, and a trailing edge.
Figure 14B:
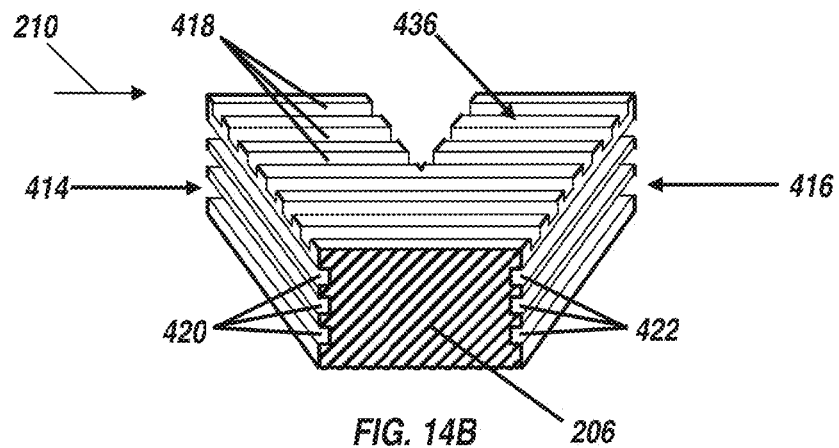
FIG. 14B is a perspective view of one embodiment of the structural member including a luminal surface, the leading edge, and the trailing edge including grooves disposed therein or thereon.

Referring to FIG. 14A, the structural member 207 includes a luminal surface 436 as well as a leading edge 414 and a trailing edge 416 relative to the direction 210 of blood flow. Referring to FIG. 14B, any or all of the luminal surface 436, the leading edge 414, and the trailing edge 416 may include grooves disposed therein or thereon. For example, in one embodiment, the luminal surface 436 may have grooves 418 disposed therein. The grooves 418 may be oriented in any direction relative to the direction 210 of blood flow; however, orientation of the grooves 418 parallel to the direction 210 of blood flow, as illustrated in FIG. 14B, exposes EC within the grooves 418 to shear stress caused by the blood flow. As noted hereinabove, such exposure of EC to shear stress increases the rate of migration of the EC.

The leading edge 414 of the structural member 406, in one embodiment, may include grooves 420 disposed therein or thereon. The grooves 420 may be oriented in any direction relative to the direction 210 of blood flow. In one embodiment as illustrated in FIG. 14B, the grooves 420 are oriented such that a component of blood flow along the leading edge 414 (for example, see the components 220 and/or 224 in FIG. 10) exposes EC within the grooves 420 to shear stress caused by the blood flow. Similarly, the trailing edge 416 of the structural member 406, in one embodiment, may include grooves 422 disposed therein or thereon. The grooves 422 may be oriented in any direction relative to the direction 210 of blood flow. In one embodiment as illustrated in FIG. 14B, the grooves 422 are oriented such that a component of blood flow along the trailing edge 416 (for example, see the component 228 in FIG. 10) exposes EC within the grooves 422 to shear stress caused by the blood flow.

It should be noted that the addition of the grooves 418, 420, 422 to one or more of the surfaces 436, 414, 416, may be instead of or in addition to any embodiment of the geometric physiologically functional features as described hereinabove with regard to FIGS. 1-9B. For example, any or all of the grooves 418, 420, 422 illustrated in FIG. 14B may be disposed in a layer or layers of vacuum deposited material including a homogeneous molecular pattern of distribution. Further, the grooves 418, 420, 422 may be disposed through one or more layers of vacuum deposited material, having differences in grain size, grain phase, and/or surface topography.

Any of the geometrically functional features or recesses may also be included in the trailing edge, leading edge, or surface regions to enhance the endothelial migration and attachment to such surfaces.

An implantable device may include problematic surfaces that may be resistant to endothelialization or may otherwise be relatively slow to endothelialize. The problematic surfaces may be disadvantaged for cell adhesion because of, for example, hemodynamic reasons such as disruption via turbulence or low shear stress (which may occur in thick stents, for example, greater than about 100 μm) or chemical reasons such as anti-mitotic and/or anti-inflammatory drugs. The problematic surfaces could be, for example, stent bridges disposed at various angles against the blood flow.

Figure 15:
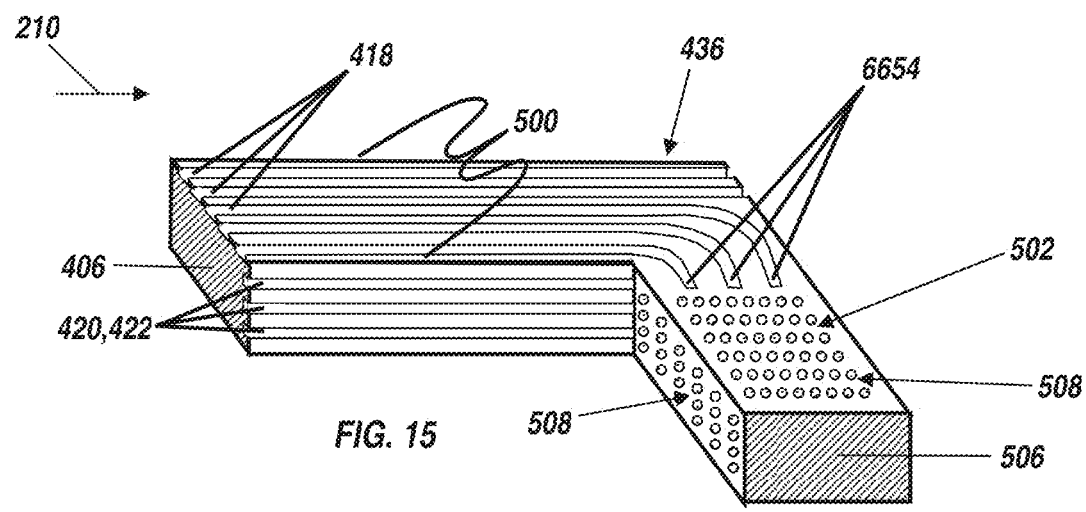
FIG. 15 is a perspective view of one embodiment of the structural member including a main highway of the grooves.

Referring to FIG. 15, it is contemplated that a combination of properly oriented grooves may facilitate EC migration to the problematic surfaces and/or promote cell stability thereon. For example, in one embodiment, a main highway 500 of the grooves 418 may be disposed in the luminal surface 436 of the structural member 406 and oriented generally parallel to the direction 210 of blood flow, as illustrated in FIG. 15. The main highway 500 could provide an abundance of migrating EC, which could be diverted therefrom to a problematic surface, for example, a surface 502 on a transversely disposed structural member 506 of the implantable device.

It is further contemplated that diversion of migrating EC from the main highway 500 could be applied to surfaces having a specific function, which may or may not otherwise be conducive to EC migration. For example, referring to FIG. 15, the structural member 506 may include surfaces including a plurality of pores 508 as might be found, for example, in a drug eluting stent.

It is contemplated that a factor in increasing endothelialization of a surface of an implanted medical device may be the cleanliness of the surface. In this context, cleanliness refers to the presence or lack of contaminant molecules bonding to otherwise unsaturated chemical bonds at the surface. A perfectly clean surface, for example as may exist in a vacuum, comprises unsaturated bonds at the surface. The unsaturated bonds provide the surface with a higher surface energy as compared to a contaminated surface having fewer unsaturated bonds.

The method disclosed herein comprehends the creation of a patterned array of geometric physiologically functional features elevated relative to a surface of an implantable biocompatible material, recessed relative to the surface, or disposed on the surface. For example, in accordance with an alternative embodiment, the implantable biocompatible material is formed of a bulk material of titanium, nickel-titanium alloy or other titanium-rich alloy metals or a top most layer of titanium, nickel-titanium alloy or other titanium-rich alloy metals deposited over the bulk material. The titanium, nickel-titanium alloy or other titanium-rich alloy metal is oxidized to convert surface titanium to titanium dioxide, then covered with a pattern-mask and exposed to high intensity UV irradiation. It is well-known that titanium dioxide ($TiO_2$) absorbs UV radiation and has been used in a variety of applications as a UV inhibitor to prevent UV transmission across a $TiO_2$ barrier layer. It has been discovered that upon exposure to UV irradiation, an originally hydrophobic and oleophilic titanium oxide layer becomes amphiphilic.

The effect of UV irradiation on a titanium oxide surface is believed to occur because of unsymmetrical cleavage of the Ti—O bond to leave $Ti^{3+}$ ions on the surface in some regions. Presently, these amphiphilic surfaces are being used in a range of technological applications, such as self-cleaning paints and anti-misting glasses. It has been recognized that these amphiphilic titanium oxide layers have use in medical applications. Zarbakhsh, A., *Characterization of photon-controlled titanium oxide surfaces, ISIS Experimental Report*, Rutherford Appelton Laboratory, May 16, 2000 (which may be found on the internet at: www.isis.rl.ac.uk/isis2001/reports/11144.pdf).

The amphiphilic state of the UV irradiated titanium oxide may be employed as an alternative to depositing patterned elevated or recessed geometric physiologically functional features onto the implantable biocompatible material. An implantable biocompatible material fabricated having a bulk substrate or a top most vacuum deposited layer of titanium or a titanium alloy is masked with a pattern mask having a plurality of openings passing there through. As with the above-described embodiment, the plurality of openings preferably have a size and special array selected to define affinity binding domains and cellular migration cites for promoting endothelial cell binding and proliferation across the substrate surface.

The open surface area of each of the plurality of openings in the pattern mask is preferably in the range of between about 1 nm to about 75 μm, and with adjacent pairs of openings being in a spaced apart relationship such that a distance of about 1 nm to about 75 μm exists between the openings, the inter-opening being greater than, about equal to, or less than the size of the opening. By interposing the pattern mask between a UV source and the surface of the implantable biocompatible material, a pattern of UV irradiated regions is imparted to the surface implantable biocompatible material, thereby altering the titanium dioxides present at the irradiated regions and forming affinity domains at the surface implantable biocompatible material.

Figure 6A:
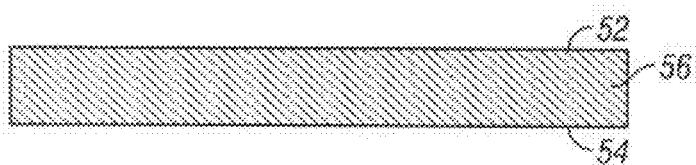
FIGS. 6A-6D are cross-sectional diagrammatic views of an embodiment, the combination of a-d representing the steps to make an inventive implantable material with chemically defined geometric physiologically functional features.

Referring to FIG. 6A, a portion of an implantable material 56 made of titanium or a titanium-alloy is shown having at least one surface 52 and 54 that is oxidized by heating or an equivalent known by the person skilled in the art.

Figure 6B:
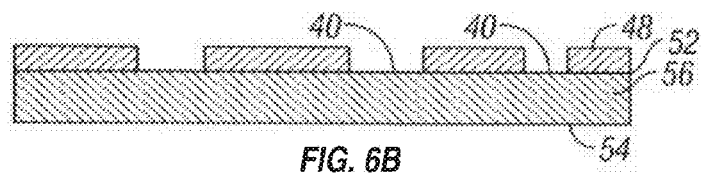

Referring to FIG. 6B, a machined mask 48 that had laser-cut holes 40 of defined size from about 1 nm to about 75 μm, from about 1 nm to about 50 μm, from about 1 nm to about 2000 nm, and preferably from about 1 nm to about 200 nm, patterned throughout to coat the at least one surface 52 of the implantable material 56 and is tightly adhered to the covered surface 52.

Figure 6C:
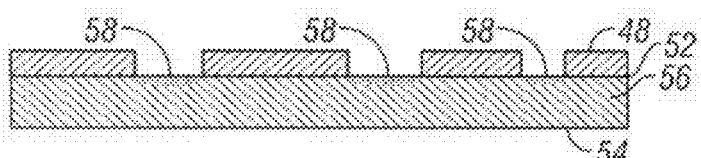

Referring to FIG. 6C, the implantable material 56 covered with the mask 48 is then illuminated by the ultraviolet rays. Because $TiO_2$ is sensitive to ultraviolet, the chemical composition of the portions 58 of the surface 52 in the holes is different from the area that is covered by the mask.

Figure 6D:
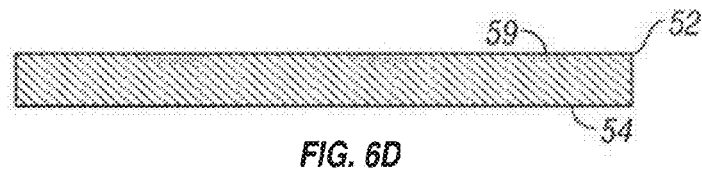

Referring to FIG. 6D, after ultraviolet irradiation, the mask is removed to reveal the surface 52 that surrounds the geometric physiologically functional features 59 formed by ultraviolet irradiation. As described above, because the shape of the holes 40 in the mask 48 could be in any of the shapes described for the geometric physiologically functional features including: circle, square, rectangle, triangle, parallel lines and intersecting lines, and combinations thereof, the geometric physiologically functional features 59 accordingly adopts such shapes also. In contrast to the geometric physiologically functional features illustrated in FIGS. 5C, 7E, 8B, and 9B, the geometric physiologically functional features 59 in FIG. 6C are not elevated and therefore have zero thickness relative to the surrounding surface of the implantable material.

Example 1

Nickel-titanium sheets were heated to oxidize titanium present at the surface of the sheet. Pattern masks fabricated from machined metal were laser drilled a pattern of holes having diameters ranging from 15 µm to 50 µm, with a single diameter of holes on each pattern mask. A single pattern mask was placed over a single nickel-titanium sheet and the assembly was exposed to high intensity ultra-violet irradiation. After UV irradiation, the irradiated nickel-titanium sheet was placed on a fully endothelialized test surface and maintained at 37° C. under simulated in vivo flow conditions and under static flow conditions. Qualitative observations were periodically made and it was found that endothelial cells bound to the pattern of UV irradiated affinity domains and migrated across the nickel-titanium sheet by proliferating across the pattern of affinity domains, eventually fully seeding endothelium on the nickel-titanium sheet.

Example 2

Human aortic EC migration onto 1×1-cm, 316L stainless steel flat coupons after fixation and Giemsa staining ECs were seeded and grown to confluence on ammonium cross-linked, firm collagen gel, covering rectangular polyester film sheet. Thin (600 µm) coupons then were implanted into endothelialized surface, such that top surface was flush with gel surface. Entire sheet then was placed into parallel plate flow chamber and exposed to fluid-imposed arterial level shear (15 dynes/cm$^2$), as shown in FIG. 16A, and low shear (1.5 dynes/cm$^2$), as shown in FIG. 16B, wall stress on right for 4 days. FIGS. 16A-16B includes an arrow indicates that direction of flow. With high shear, all cell migration occurs in direction of flow. At low shear, migration is diminished and in all directions.

In static culture conditions, the rate of EC migration on a metal surface such as stainless steel or nitinol is initially 10 µm/h and increases to 15 µ/h 10 days later. In the presence of flow at normal shear rates, the migration rate increases to 25 m/h by 7 days. With normal shear, ECs migrate in the direction of flow with little migration observed against flow. With low shear, migration is slower and tends to occur in every direction, as shown in FIGS. 16A-16B. This observation agrees with the fact that coronary stents placed with minimal injury to the endothelium may require only a few days to endothelialize. In contrast, in stents placed in totally occluded vessels or after large endothelial injury, such as after catheter endarterectomy or laser revascularization, endothelializaton time may be prolonged from several weeks to a few months.

In addition to flow shear, the topography of the surface plays a role in EC coverage. An obstacle raised above the plane of the vessel's inner surface, such as an intravascular stent, hinders cell progression in a manner proportional to its height. Because stents have complex geometries, an experimental model of a stent was made with simple shapes of flat material with a thickness commensurate with the thickness of vascular stents. Pieces of progressively increasing heights from 25 to 250 µm were placed on a monolayer of ECs in a laminar flow chamber at physiologic wall shear stress (15 dynes/cm$^2$). The number of cells able to gain access on top of the obstacles decreased significantly with heights of 100 µm and greater as compared with 25 µm. No cells were found on top of 250 µm-thick obstacles, as shown in FIG. 17. These experimental results agree with clinical experience with intravascular stents having increased failure rates with increasing wall thickness. Two coronary stents of identical design and wall thicknesses of 50 and 140 µm encountered significantly higher clinical and angiographic restenosis rates with the later. This reflects impaired endothelialization and increased intimal formation with the larger obstacles caused by thicker stent struts.

Figure 18:
FIG. 18 is a photograph of human aortic ECs migrating on stainless steel in direction of arrow stained with Giemsa and 200× magnification; confluent human aortic ECs were allowed to migrate from firm collagen gel onto implanted 1×1-cm flat stainless steel coupons with static culture conditions for 7 days; on encounter with surface scratch, cells deviate to follow feature; and three cells in middle of field are aligned on single scratch.
Figure 19:
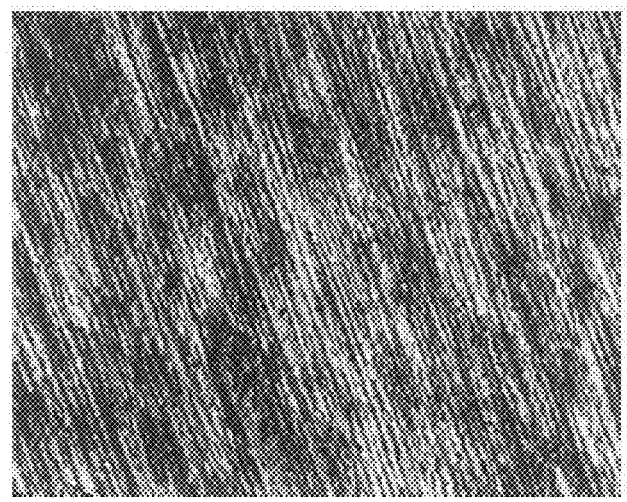
FIG. 19 is a photograph of human aortic ECs migrating on uniformly scratched stainless steel surface and stained with Giemsa stain at 200× magnification; cells migrated from confluent human aortic EC covered gel onto flat stainless steel coupons as described previously; and parallel scratch pattern was created with 320-grain carbide sand paper.
Figure 20:
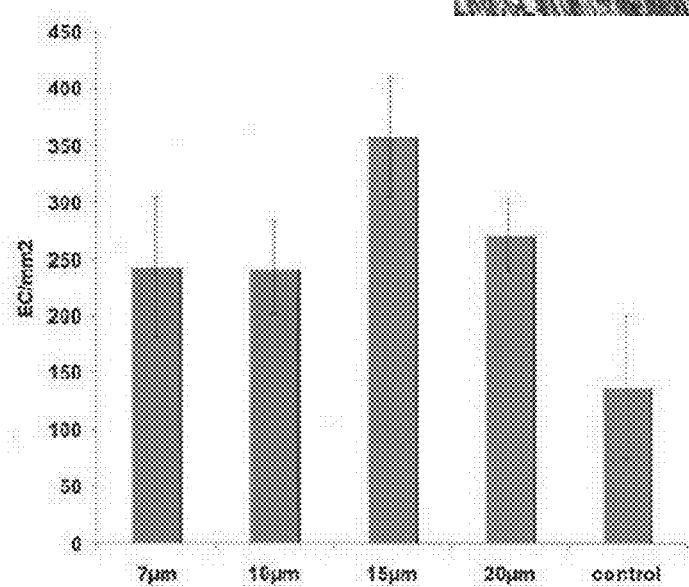
FIG. 20 is a graph showing Bars which indicate mean number of ECs per mm$^2$ on stainless steel microfabricated surfaces, with square section grooves from 7 to 20 µm wide; grooves of defined width were created with photolithographic process; grooved stainless steel 1×1-cm coupons were implanted on endothelialized gel surface as described below, and cells were allowed to migrate onto surface for 7 days with static culture conditions; control indicates flat surface; and surface with 15-µm grooves has significantly larger cell population.
Figure 21A:
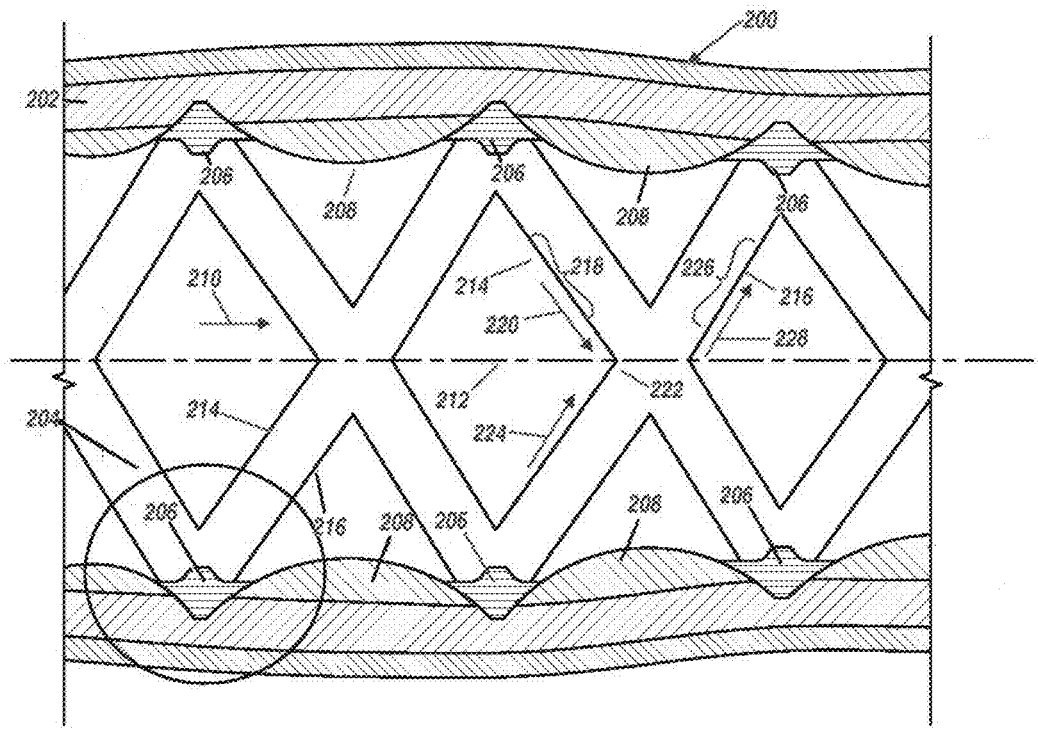
FIG. 21A is a cross-sectional view of an artery having an arterial wall including an implantable medical device.
Figure 21B:
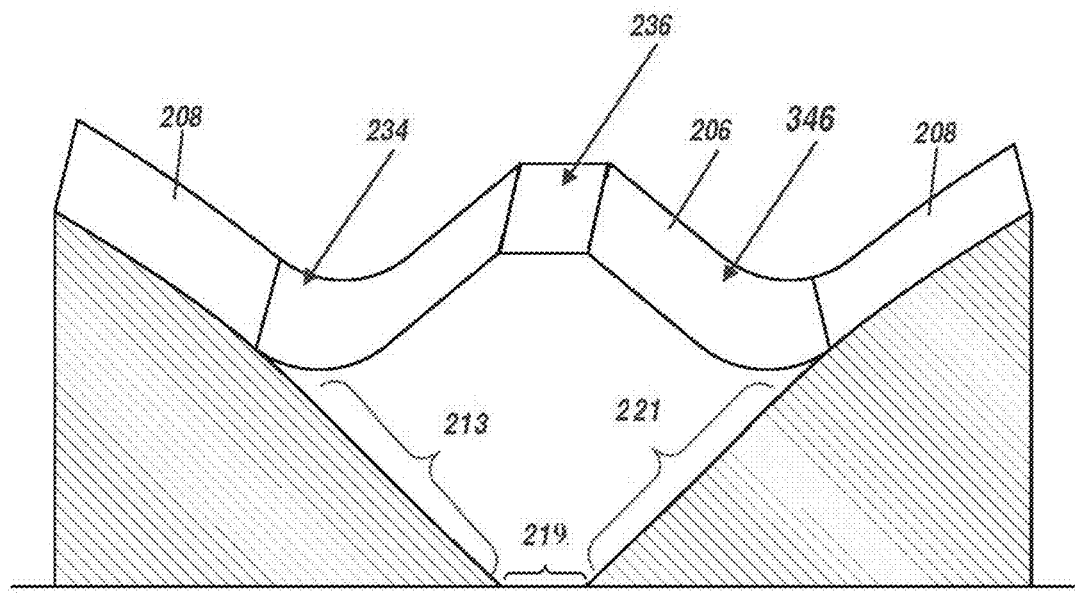
FIG. 21B is an enlarged perspective transverse cross-sectional view from circle 21B in FIG. 21A of the implantable medical device, in accordance with one embodiment.
Figure 22A:
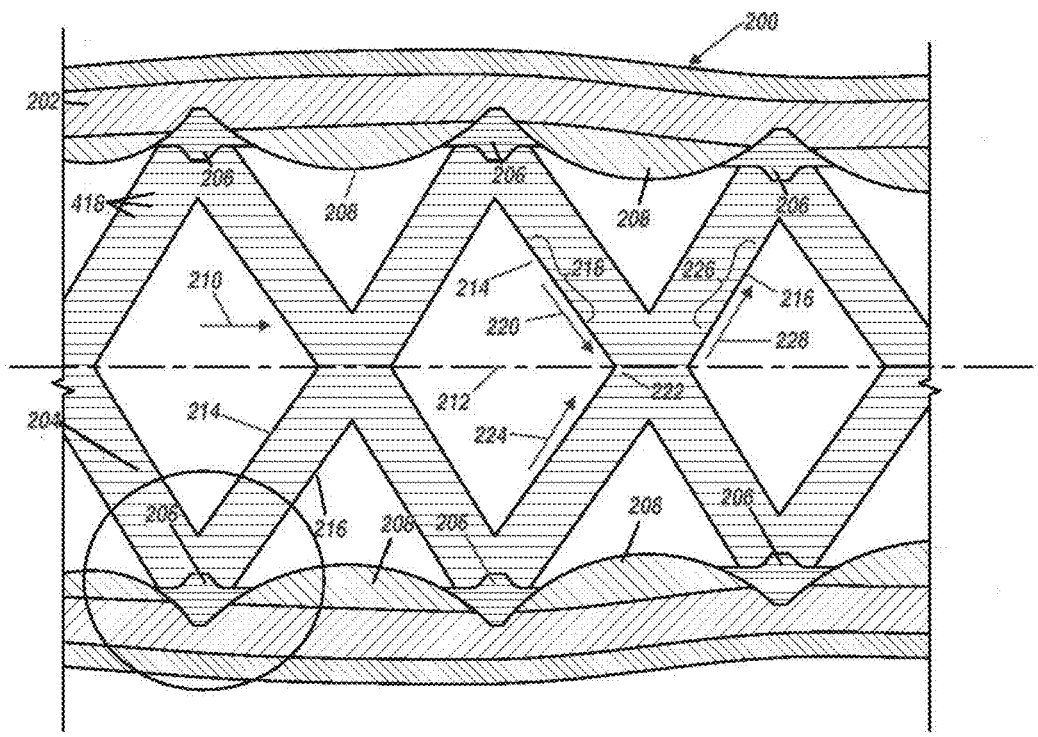
FIG. 22A is a cross-sectional view of an artery having an arterial wall including an implantable medical device.
Figure 22B:
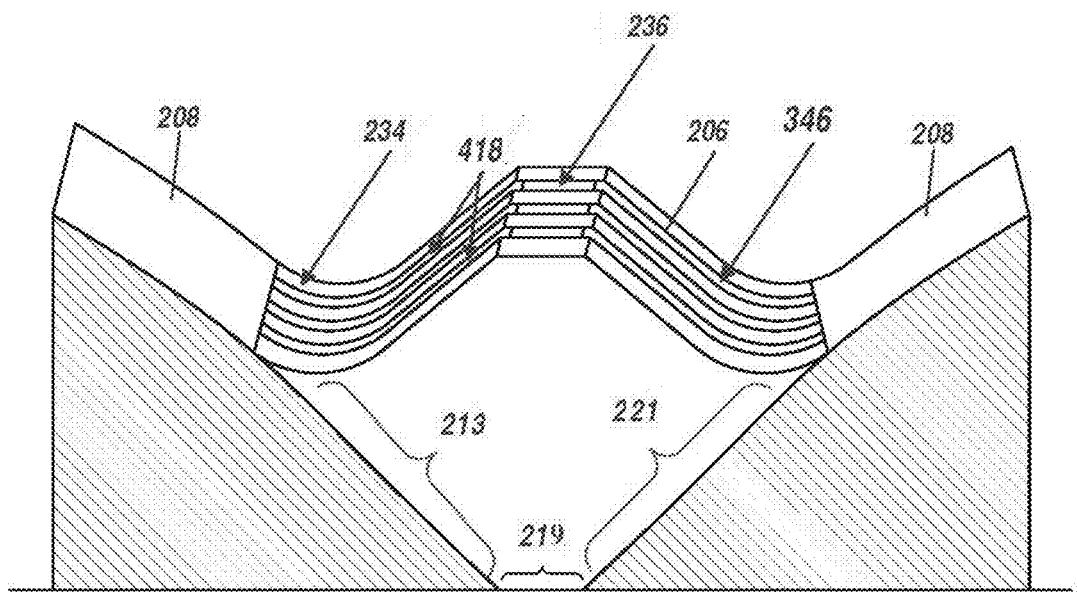
FIG. 22B is an enlarged perspective transverse cross-sectional view from circle 22B in FIG. 22A of the implantable medical device, in accordance with one embodiment.

With slow motion video recordings of ECs migrating on a flat surface under flow, cells migrate downstream not in straight lines but rather in a zigzag pattern. This motion increases the probability of encounter with other migrating cells. Cell collisions reduce migration speed by contact inhibition. Multiple collisions halt migration and allow confluence. If a migrating cell encounters a linear feature on the surface, such as a scratch disposed at an angle to the direction of flow, it follows the feature, as shown in FIG. 18. If multiple parallel scratches are made on the surface, the cells migrate in straight lines along the scratches, as shown in FIG. 19. The migration speed is thus increased because the side to side movement is inhibited. The increase in migration speed reflected on the cell count on the leading edge of the material is dependent on the width of the grooves, as it relates to cell size, as shown in FIG. 20. Narrow grooves prevent cell progression, and excessively large grooves allow the cells to wander, therefore slowing down migration speed. With stents with microscopic parallel grooves created on the inner surface, significantly accelerated endothelialization rates were found in carotid artery stents of pigs 1 week after placement. With the hypothetic assumption that no endothelial damage is produced by the stent placement, ECs adjacent to the raised stent struts slough because of superficial microflow disturbances. This is shown experimentally by measuring the area devoid of ECs shortly after placement of geometric obstacles on an EC monolayer. The angle of the sides of the object relative to the flow direction influences the extent of endothelial slough. The lowest EC loss is observed adjacent to the edges along the flow, and the largest on the down flow side of edges disposed transversely. Intermediate degrees of EC loss were found on the transverse upstream edge and on the 45-degree edge. This finding supports the clinical experience of higher restenosis rates for coiled stents with struts substantially perpendicular to the direction of flow.

The influence of the edge angle of stent struts in the vertical axis (radial direction in a vessel lumen) also was evaluated. Shallow angles in objects disposed perpendicular to flow allowed the largest number of cells to migrate on top of the obstacle. This observation indicates that stent struts should have blunted edges or, even better, a trapezoidal cross section as indicated above.

The density of the stent mesh has an influence on the intimal hyperplastic response. Stents with few struts spaced far apart produce more intimal hyperplasia than more struts around the circumference if they are evenly distributed. This is related to wall indentation with a few stent struts producing a polygonal rather than a circumferential lumen. However, increased strut density may come at the price of larger metal surface, and this in turn may affect patency. Of course, the many variables influenced by stent design, such as total metal surface, radiopacity, radial strength, expandability ratio, shortening, and flexibility, affect each other. Typically, compromises must be reached to attain the best possible results within technical limitations.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the implantable medical device having enhanced endothelial migration features described herein and to teach the best mode of carrying out the same.

I claim:

1. A tubular implantable medical device having enhanced endothelial migration features, comprising:
    a plurality of structural members,
    each of the plurality of structural members having an irregular polygonal transverse cross-sectional profile,
    wherein each facet of the irregular polygonal transverse cross-sectional profile defines a surface of the plurality of structural members,
    wherein the defined surfaces of the plurality of structural members make up abluminal surfaces engaged with a vessel and luminal surfaces exposed to a blood flow,
    wherein the luminal surfaces form a transverse cross-sectional profile comprising a concave curvilinear second surface region and a concave curvilinear fourth surface region, the second surface region and the fourth surface region being interconnected by an intermediate generally planar third surface region;
    wherein at least the third surface region comprises at least one groove disposed within the third surface region, the groove generally parallel to the direction of blood flow.

2. The tubular implantable medical device of claim 1, wherein the shear stress generated at the second surface region is between about 5 and 25 dynes/cm2.

3. The tubular implantable medical device of claim 1, wherein the second surface region includes a radius curvature Rs, wherein Rs is between about 1 nm to about 75 mm.

4. The tubular implantable medical device of claim 3, wherein the second surface region joins an abluminal surface to form an angle As, wherein the angle As is less than 90 degrees, wherein at least one surface includes a plurality of pores.

5. The tubular implantable medical device of claim 4, wherein second surface region joins the third surface region to an angle At, wherein the angle At is greater than 90 degrees.

6. The tubular implantable medical device of claim 5, wherein a length of the third surface region is less than a length of the second surface region.

7. The tubular implantable medical device of claim 6, wherein the abluminal surfaces further comprise a first abluminal surface joining a second abluminal surface and the second abluminal surface joining a third abluminal surface, whereby the third abluminal surface joins the fourth surface region to form a substantially hexagonal cross-section configuration of the structural member.

8. The tubular implantable medical device of claim 7, wherein the fourth surface region includes a radius curvature Rs, wherein Rs is between about 1 nm to about 75 mm.

9. The tubular implantable medical device of claim 8, wherein the fourth surface region joins the third abluminal surface to form an angle Ar, wherein the angle Ar is less than 90 degrees.

10. The tubular implantable medical device of claim 9, wherein fourth surface region joins the third surface region to an angle As, wherein the angle As is greater than 90 degrees.

11. The tubular implantable medical device of claim 10, wherein the length of the third surface region is less than a length of the fourth surface region.

12. The tubular implantable medical device of claim 11, wherein the second surface region and the fourth surface region include a plurality of geometric physiologically functional features including a focal adhesion point for affinity binding of endothelial cells.

13. The implantable medical device of claim 11, wherein the at least one groove is between 7 to 20 μm wide.

14. A method of forming a tubular implantable medical device having enhanced endothelial migration features, comprising:
    forming a tubular structure comprising of structural members, the tubular structure having a central longitudinal axis;
    forming the structural members to include a transverse cross-sectional profile comprising a first surface region joined to a concave curvilinear second surface region, the second surface region joined to a generally planar third surface region, the third surface region joined to a concave curvilinear fourth surface region, the fourth surface region joined to a fifth surface region, the fifth surface region joined to a sixth surface region; and
    whereby the tubular implantable medical device includes at least one groove disposed across at least one of the second surface region, the third surface region, and the fourth surface region, the at least one groove being oriented generally parallel to the central longitudinal axis of the tubular structure.

15. The method of claim 14, further comprising forming the second surface region to include includes a radius curvature Rs, wherein Rs is between about 1 nm to about 75 mm.

16. The method of claim 15, further comprising joining the second surface region to the first surface region to form an angle As, wherein the angle As is less than 90 degrees, wherein at least one surface including a plurality of pores.

17. The method of claim 16, further comprising joining the second surface region to the third surface region at an angle At, wherein the angle At is greater than 90 degrees.

18. The method of claim 17, further comprising joining the first surface region to the second surface region, the second surface region to the third surface region, the third surface region to the fourth surface region, the fourth surface region to the fifth surface region, the fifth surface region to the sixth surface region to form a substantially hexagonal cross-section configuration of the structural member.

19. The method of claim 18, wherein the fourth surface region includes a radius curvature Rs, wherein Rs is between about 1 nm to about 75 mm.

20. The method of claim 19, further comprising joining the fourth surface region to the fifth surface region to form an angle Ar, wherein the angle Ar is less than 90 degrees.

\* \* \* \* \*